US011311729B2

(12) United States Patent
Davies et al.

(10) Patent No.: US 11,311,729 B2
(45) Date of Patent: Apr. 26, 2022

(54) TITRATION FOR SUB-THRESHOLD ELECTRICAL STIMULATION THERAPY

(71) Applicant: Medtronic, Inc., Minneapolis, MN (US)

(72) Inventors: Lachlan Davies, Minneapolis, MN (US); Sheryl McCammon, North Oaks, MN (US); Andrew J. Cleland, St. Paul, MN (US); Melanie D Goodman Keiser, Otsego, MN (US); Ye Tan, Shoreview, MN (US); Lisa M. Johanek, White Bear Lake, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 54 days.

(21) Appl. No.: 16/797,065

(22) Filed: Feb. 21, 2020

(65) Prior Publication Data
US 2021/0031033 A1 Feb. 4, 2021

Related U.S. Application Data

(60) Provisional application No. 62/880,493, filed on Jul. 30, 2019.

(51) Int. Cl.
*A61N 1/36* (2006.01)

(52) U.S. Cl.
CPC ....... *A61N 1/3615* (2013.01); *A61N 1/36071* (2013.01); *A61N 1/36139* (2013.01); *A61N 1/36175* (2013.01)

(58) Field of Classification Search
None
See application file for complete search history.

(56) References Cited

U.S. PATENT DOCUMENTS

| 8,989,861 B2 | 3/2015 | Su et al. |
| 9,089,699 B2 | 7/2015 | Su et al. |
| 9,168,374 B2 | 10/2015 | Su |

(Continued)

FOREIGN PATENT DOCUMENTS

| WO | 2011/156288 A1 | 12/2011 |
| WO | 2014/197564 A1 | 12/2014 |

(Continued)

OTHER PUBLICATIONS

Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21, Dec. 2017, pp. 67-76.

(Continued)

*Primary Examiner* — Paula J Stice
(74) *Attorney, Agent, or Firm* — Shumaker & Sieffert, P.A.

(57) ABSTRACT

In some examples, a medical device is configured to deliver sub-threshold electrical stimulation therapy to a patient at a stimulation intensity that is significantly less than a perception or paresthesia threshold intensity level for the patient. The medical device may determine the particular intensity level for the patient through a titration process. The medical device may titrate automatically or based upon the input of the patient, a clinician or a physician.

19 Claims, 13 Drawing Sheets

(56) References Cited

U.S. PATENT DOCUMENTS

| | | | |
|---|---|---|---|
| 9,409,020 | B2 | 8/2016 | Parker |
| 9,724,509 | B2 | 8/2017 | Su et al. |
| 10,149,978 | B1 | 12/2018 | Park |
| 10,518,086 | B2 | 12/2019 | Su et al. |
| 10,576,282 | B2 | 3/2020 | Doan et al. |
| 2007/0100388 | A1 | 5/2007 | Gerber |
| 2009/0054950 | A1 | 2/2009 | Stephens |
| 2013/0079841 | A1 | 3/2013 | Su et al. |
| 2014/0277256 | A1* | 9/2014 | Osorio .............. A61N 1/36053 607/45 |
| 2015/0032181 | A1* | 1/2015 | Baynham ........... A61N 1/37241 607/46 |
| 2015/0148878 | A1 | 5/2015 | Yoo et al. |
| 2015/0217116 | A1* | 8/2015 | Parramon .......... A61N 1/36071 607/59 |
| 2015/0328454 | A1 | 11/2015 | Lambert |
| 2016/0114167 | A1 | 4/2016 | Jiang et al. |
| 2016/0339250 | A1 | 11/2016 | Kaula et al. |
| 2017/0239470 | A1 | 8/2017 | Wei et al. |
| 2017/0291031 | A1 | 10/2017 | Lee |
| 2018/0035924 | A1 | 2/2018 | Gunderson et al. |
| 2018/0056073 | A1 | 3/2018 | Torgerson |
| 2018/0078769 | A1 | 3/2018 | Dinsmoor et al. |
| 2018/0133484 | A1 | 5/2018 | Dinsmoor et al. |
| 2018/0369592 | A1 | 12/2018 | Johanek |
| 2019/0001135 | A1 | 1/2019 | Yoo et al. |
| 2019/0009098 | A1 | 1/2019 | Jiang et al. |
| 2019/0046800 | A1 | 2/2019 | Doan et al. |
| 2019/0060647 | A1 | 2/2019 | Su et al. |
| 2019/0184168 | A1 | 6/2019 | Vansickle et al. |
| 2019/0269924 | A1 | 9/2019 | Su et al. |
| 2020/0078594 | A1 | 3/2020 | Jiang et al. |
| 2021/0031032 | A1 | 2/2021 | Zirpel et al. |
| 2021/0031033 | A1* | 2/2021 | Davies .............. A61N 1/36175 |
| 2021/0031041 | A1 | 2/2021 | Davies et al. |
| 2021/0031042 | A1 | 2/2021 | Davies et al. |

FOREIGN PATENT DOCUMENTS

| | | | |
|---|---|---|---|
| WO | 2017/106539 | A1 | 6/2017 |
| WO | 2018/089418 | A1 | 5/2018 |
| WO | 2018080753 | A1 | 5/2018 |

OTHER PUBLICATIONS

Elterman et al., "The Novel Axonics® Rechargeable Sacral Neuromodulation System: Procedural and Technical Impressions from an Initial North American Experience," Neurourology and Urodynamics, Feb. 2018, 8 pp.

Amundsen et al., "Sacral Neuromodulation for Intractable Urge Incontinence: Are There Factors Associated With Cure?," Adult Urology, vol. 66, No. 4, Oct. 2005, pp. 746-750.

Janknegt et al., Improving Neuromodulation Technique for Refractory Voiding Dysfunctions: Two-Stage Implant, Adult Urology, vol. 49, No. 3, Mar. 1997, pp. 358-362.

Peters et al., "The Relationship Between Subjective and Objective Assessments of Sacral Neuromodulation Effectiveness in Patients with Urgency-Frequency," Neurourology and Urodynamics, vol. 27, No., Nov. 2008, 775-778.

Scheepens et al., "Predictive Factors for Sacral Neuromodulation in Chronic Lower Urinary Tract Dysfunction," Adult Urology, vol. 60, No. 4. Oct. 2002, pp. 598-602.

Schmidt et al., "Sacral Nerve Stimulation for Treatment of Refractory Urinary Urge Incontinence," Sacral Nerve Stimulation Study Group. The Journal of Urology, vol. 162, No. 2, Aug. 1999, pp. 352-357.

Siegel et al., "Long-Term Results of a Multicenter Study on Sacral Nerve Stimulation for Treatment of Urinary Urge Incontinence, Urgency-Frequency, and Retention," Urology, vol. 56, No. 6, Supp. 6A, Dec. 4, 2000, pp. 87-91.

Noblett et al., "Results of a Prospective, Multicenter Study Evaluating Quality of Life, Safety, and Efficacy of Sacral Neuromodulation at Twelve Months in Subjects with Symptoms of Overactive Bladder," Neurourology and Urodynamics, Dec. 24, 2014, pp. 246-251.

Medtronic. InterStim® Therapy InterStim® II Model 3058 Neurostimulator InterStim® Model 3023 Neurostimulator Implant manual MA12231A010 ed2012., May 2012, 32 pp.

Medtronic. Interstim® Therapy N'Vision® Model 8840 Clinician Programmer and Model 8870 Application Card Programming Guide for Software Version B 05/08 supporting InterStim® II Model 3058 and InterStim® Model 3023 Neurostimulators. M220804A004 ed2008., 2008 ((Applicant points out, in accordance with MPEP 609.04(a), that the year of publication, 2008, is sufficiently earlier than the effective U.S. filing date, so that the particular month of publication is not in issue.), 160 pp.

Su et al., "Neuromodulation in a Rat Model of the Bladder Micturition Reflex," American Journal of Physiology, vol. 302, No. 4, Feb. 15, 2012, pp. F477-F486.

Peters et al., "Randomized Trial of Percutaneous Tibial Nerve Stimulation Versus Sham Efficacy in the Treatment of Overactive Bladder Syndrome: Results from the SUmiT Trial," The Journal of Urology, vol. 183, No. 4, Apr. 2010, pp. 1438-1443.

Peters et al., "Effect of Sacral Neuromodulation Rate on Overactive Bladder Symptoms: A Randomized Crossover Feasibility Study," Lower Urinary Tract Symptoms, Vol. vol. 5, No. 3, Sep. 2013, pp. 129-133.

"Guideline on Adjustment for Baseline Covariates in Clinical Trials," European Medicines Agency, Feb. 26, 2015, 11 pp.

Amend et al., How Does Sacral Modulation Work Best? Placement and Programming Techniques to Maximize Efficacy. Current Urology Reports, vol. 12, No. 5, Oct. 2011, pp. 327-335.

Maxwell et al., "Reprogramming Requirements After Sacral Nerve Stimulator Implantation: Correlation with Preoperative Indication," The Journal of Urology, vol. 179, No. 2, Feb. 2008, pp. 549-551.

Altomare et al., The Effects of Sacral Nerve Stimulation on Continence are Temporarily Maintained After Turning the Stimulator Off, Coloretcal Disease, vol. 15, No. 12, Dec. 2013, pp e741-e748.

Hoen et al., "Intermittent Sacral Neuromodulation for Idiopathic Urgency Urinary Incontinence in Women," Neurourology and Urodynamics, vol. 36, Feb. 2017, pp. 385-389.

Marcelissen et al., "The Effect of Pulse Rate Changes on the Clinical Outcome of Sacral Neuromodulation," The Journal of Urology, vol. 185, No. 5, May 2011, pp. 1781-1785.

Markle et al., "Prospective Randomized Crossover Trial Comparing Continuous and Cyclic Stimulation in InterStim Therapy," Female Pelvic Medicine & Reconstructive Surgery, vol. 21, No. 6, Nov.-Dec. 2015, pp. 355-358.

Michelsen et al., "A Prospective, Randomized Study: Switch Off The Sacral Nerve Stimulator During the Night?," Diseases of the Colon and Rectum, vol. 51, No. 5, Jun. 2008, pp. 538-540.

Worsoe et al., "Turning Off Sacral Nerve Stimulation Does Not Affect Gastric and Small Intestinal Motility in Patients Treated for Faecal Incontinence," Colorectal Disease, vol. 14, No. 10, Oct. 2012, pp. 713-720.

Snellings et al., "Effects of Stimulation Site and Stimulation Parameters on Bladder Inhibition by Electrical Nerve Stimulation," BJU International, vol. 110, No. 1, Jul. 2012, pp. 136-143.

Zhang et al., "Neural Pathways Involved in Sacral Neuromodulation of Reflex Bladder Activity in Cats," American Journal of Physiology, Renal Physiology, vol. 304, No. 6, Mar. 15, 2013, pp. F710-F717.

Mahfooz et al., Parameters of Successful Sacral Root Neuromodulation of the Pelvic Floor: a Retrospective Study, The Canadian Journal of Urology, vol. 11, No. 3, Jun. 2004, pp. 2303-2308.

Cadish et al., "Stimulation Latency and Comparison of Cycling Regimens in Women Using Sacral Neuromodulation," Neurourology and Urodynamics, vol. 36, Feb. 1, 2016, pp. 486-489.

"InterStim® Therapy, Programming Pointers, N'Vision® Clinician Programmer," by Medtronic, UC200604277 EN NI7249, 2006, 150 pp. (Applicant points out, in accordance with MPEP 609.04(a), that

(56) References Cited

OTHER PUBLICATIONS the year of publication, 2006, is sufficiently earlier than the effective U.S. filing date, so that the particular month of publication is not in issue.).

Beer et al., "Cycling Versus Continuous Mode in Neuromodulator Programming: A Crossover Randomized Control Trial," Urologic Nursing, Vo. 36, No. 3, May-Jun. 2016, 16 pp.

Burton et al., "Effectiveness of Percutaneous Posterior Tibial Nerve Stimulation for Overactive Bladder: A Systematic Review and Meta-Analysis," Neurourology and Urodynamics, vol. 31, No. 8, Nov. 2012, 11 pp.

Oerlemans et al., "Is on-Demand Sacral Neuromodulation in Patients With OAB Syndrome a Feasible Therapy Regime?", Neurourology and Urodynamics, vol. 30, No. 8, Nov. 2011, 4 pp.

Price et al., "Prospective Randomized Crossover Trial Comparing Continuous and Cyclic Stimulation in InterStim Therapy", Female Pelvic Medicine & Reconstructive Surgery, vol. 21, No. 6, Nov./Dec. 2015, 4 pp.

Siegel et al., "Prospective Randomized Feasibility Study Assessing the Effect of Cyclic Sacral Neuromodulation on Urinary Urge Incontinence in Women," Female Pelvic Medicine & Reconstructive Surgery, vol. 00, No. 00, Mar. 2017, 5 pp.

Su et al., "Electromyographic Response Across Different Pulse-Widths of Sacral Neuromodulation in Sleep," Neuromodution: Technology at the Neural Interface, vol. 22, No. 6, Feb. 2018, 6 pp.

Van Der Pal et al., "Percutaneous tibial nerve stimulation in the treatment of refractory overactive bladder syndrome: is maintenance treatment necessary?," BJU International, vol. 97, No. 3, Mar. 2006, 4 pp.

U.S. Appl. No. 16/797,093, filed Feb. 21, 2020, naming inventors Davies et al.

U.S. Appl. No. 16/797,115, filed Feb. 21, 2020, naming inventors Davies et al.

U.S. Appl. No. 16/942,542, filed Jul. 29, 2020, naming inventors Zirpel et al.

International Search Report and Written Opinion of International Application No. PCT/US2020/037718, dated Sep. 3, 2020, 15 pp.

Office Action from U.S. Appl. No. 16/797,093, dated Jun. 23, 2021, 5 pp.

Office Action from U.S. Appl. No. 16/797,115, dated Jul. 21, 2021, 6 pp.

Office Action from U.S. Appl. No. 16/797,093, dated Sep. 29, 2021, 9 pp.

Response to Office Action dated Jul. 21, 2021, from U.S. Appl. No. 16/797,115, filed Oct. 21, 2021, 4 pp.

Response to Office Action dated Jun. 23, 2021, from U.S. Appl. No. 16/797,093, filed Sep. 20, 2021, 9 pp.

Final Office Action from U.S. Appl. No. 16/797,093, dated Sep. 29, 2021, 9 pp.

Response to Office Action dated Sep. 29, 2021, from U.S. Appl. No. 16/797,093, filed Nov. 29, 2021, 10 pp.

Advisory Action from U.S. Appl. No. 16/797,093, dated Jan. 13, 2022, 3 pp.

Final Office Action from U.S. Appl. No. 16/797,115, dated Dec. 22, 2021, 7 pp.

International Preliminary Report on Patentability from International Application No. PCT/US2020/037718, dated Feb. 10, 2022, 9 pp.

Office Action from U.S. Appl. No. 16/797,093, dated Feb. 15, 2022, 8 pp.

Response to Advisory Action dated Jan. 13, 2022, from U.S. Appl. No. 16/797,093, filed Jan. 28, 2022, 9 pp.

Response to Final Office Action dated Dec. 22, 2021, from U.S. Appl. No. 16/797,115, filed Feb. 9, 2022, 11 pp.

\* cited by examiner

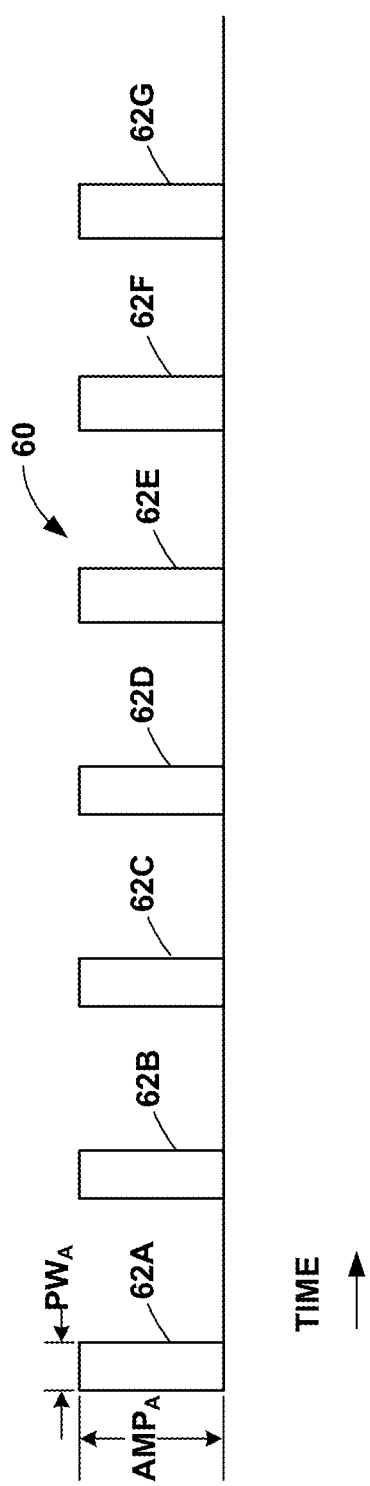
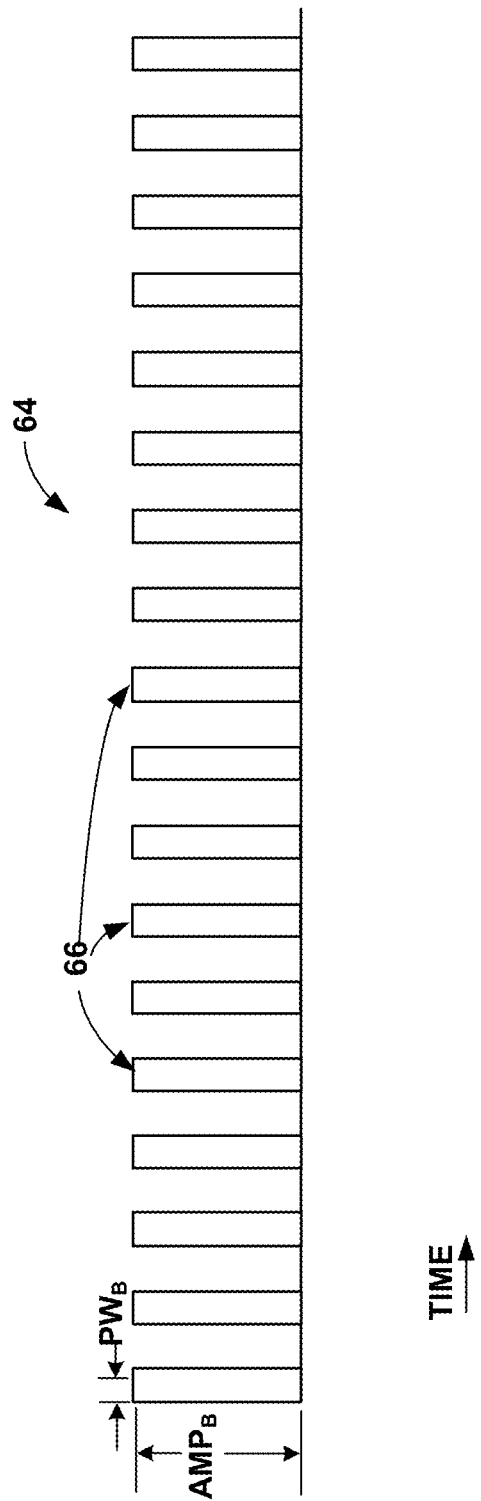

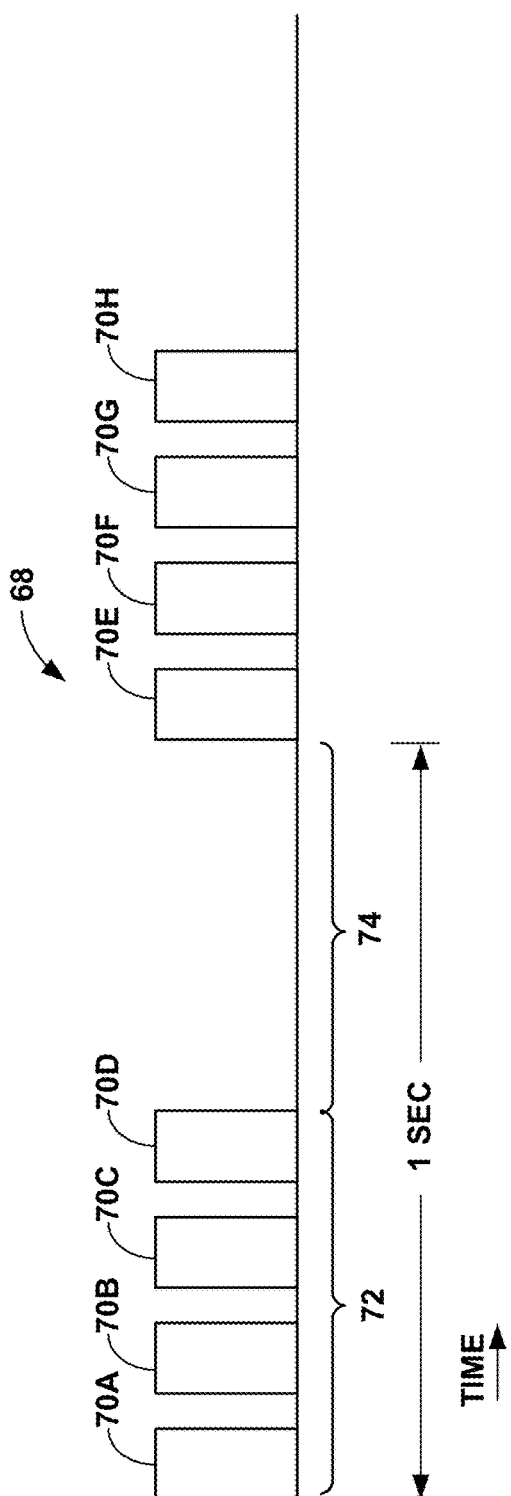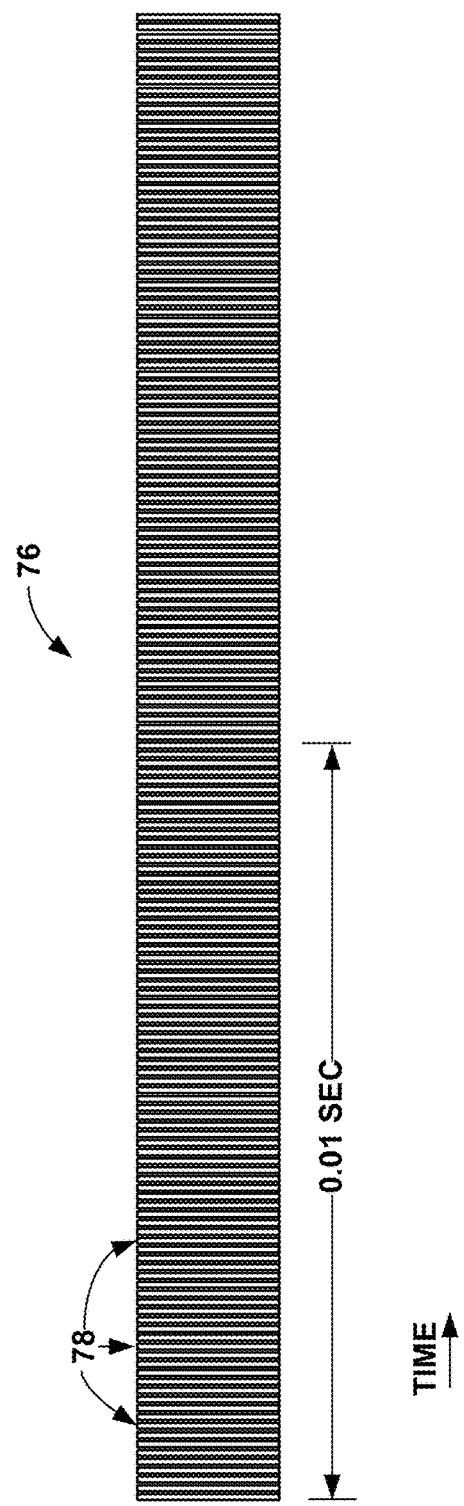

TITRATION FOR SUB-THRESHOLD ELECTRICAL STIMULATION THERAPY

This application claims the benefit of U.S. Provisional Application No. 62/880,493 entitled SUB-THRESHOLD ELECTRICAL STIMULATION THERAPY, filed Jul. 30, 2019, the entirety of which is hereby incorporated by reference.

TECHNICAL FIELD

The disclosure relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, sexual dysfunction, obesity, or gastroparesis. A medical device may deliver electrical stimulation therapy via one or more leads that include electrodes located proximate to target locations associated with the brain, the spinal cord, peripheral nerves, or the gastrointestinal tract of a patient. Hence, electrical stimulation may be used in different therapeutic applications, such as spinal cord stimulation (SCS), deep brain stimulation (DBS), gastric stimulation, or peripheral nerve field stimulation (PNFS).

A physician or clinician may select values for a number of programmable parameters in order to define the electrical stimulation therapy to be delivered by the implantable stimulator to a patient. For example, the physician or clinician may select one or more electrodes, a polarity of each selected electrode, a voltage or current amplitude, a pulse width, and a pulse frequency as stimulation parameters. A set of therapy parameters, such as a set including electrode combination, electrode polarity, amplitude, pulse width and pulse frequency, may be referred to as a therapy program in the sense that they define the electrical stimulation therapy to be delivered to the patient.

SUMMARY

This disclosure describes example medical devices, systems, and techniques for delivering sub-threshold electrical stimulation therapy to a patient to treat one or more patient conditions, such as chronic back and/or leg pain (e.g., using SCS). As used herein, sub-threshold refers to electrical stimulation at an intensity that is lower than a patient's paresthesia or perception threshold. A patient's paresthesia threshold is also described herein as a "paresthesia level" or a "threshold paresthesia intensity level". A patient's perception threshold is also described herein as a "perception level" or a "threshold perception intensity level". A patient's paresthesia threshold and a patient's perception threshold are described below. In some examples, a medical device is configured to deliver the sub-threshold electrical stimulation therapy by at least generating and delivering an electrical stimulation signal with intensity that is significantly less than a paresthesia or perception threshold of the patient (e.g., less than 80%, 60%, 40%, or 20% of the paresthesia or perception threshold of the patient). The electrical stimulation therapy may comprise stimulation pulses that may each have relatively low intensity as compared with the paresthesia or perception threshold. In some examples, the sub-threshold electrical stimulation therapy is delivered to particular physiological geometries of a patient. In other examples, a paresthesia or perception threshold in a posture of a patient may be used to predict a paresthesia or perception threshold in a different posture of the patient. The electrical stimulation delivered to the patient may be high enough to elicit a therapeutic response from the patient even at relatively low intensities.

In one example, a method according to the techniques of this disclosure includes generating, by a medical device, a lower intensity electrical stimulation signal comprising a plurality of pulses, wherein the lower intensity electrical stimulation signal has a stimulation intensity that is less than or equal to 40% of a paresthesia threshold or perception threshold of a patient; and delivering, by the medical device, the lower intensity electrical stimulation signal to the patient.

In another example, a system according to the techniques of this disclosure includes a stimulation generator configured to generate and deliver electrical stimulation therapy to a patient via at least one electrode; and a processor configured to control the stimulation generator to: generate a lower intensity electrical stimulation signal comprising a plurality of pulses, wherein the lower intensity electrical stimulation signal has a stimulation intensity that is less than or equal to 40% of a paresthesia threshold or perception threshold of the patient; and deliver the lower intensity electrical stimulation signal to the patient.

In another example according to the techniques of this disclosure, a non-transitory computer-readable medium includes instructions that, when executed by a processor, cause the processor to: control a stimulation generator to generate a lower intensity electrical stimulation signal comprising a plurality of pulses; the lower intensity electrical stimulation signal having a stimulation intensity that is less than or equal to 40% of a paresthesia threshold or perception threshold of the patient; and control the stimulation generator to deliver the lower intensity electrical stimulation signal to the patient.

The details of one or more examples are set forth in the accompanying drawings and the description below. Other features, objects, and advantages of examples according to this disclosure will be apparent from the description and drawings, and from the claims.

BRIEF DESCRIPTION OF DRAWINGS

FIGS. 4 and 5 illustrate an example of electrical stimulation waveforms.

FIG. 6 illustrates an example burst electrical stimulation waveform.

FIG. 7 illustrates an example high frequency electrical stimulation waveform.

DETAILED DESCRIPTION

Figure 1:
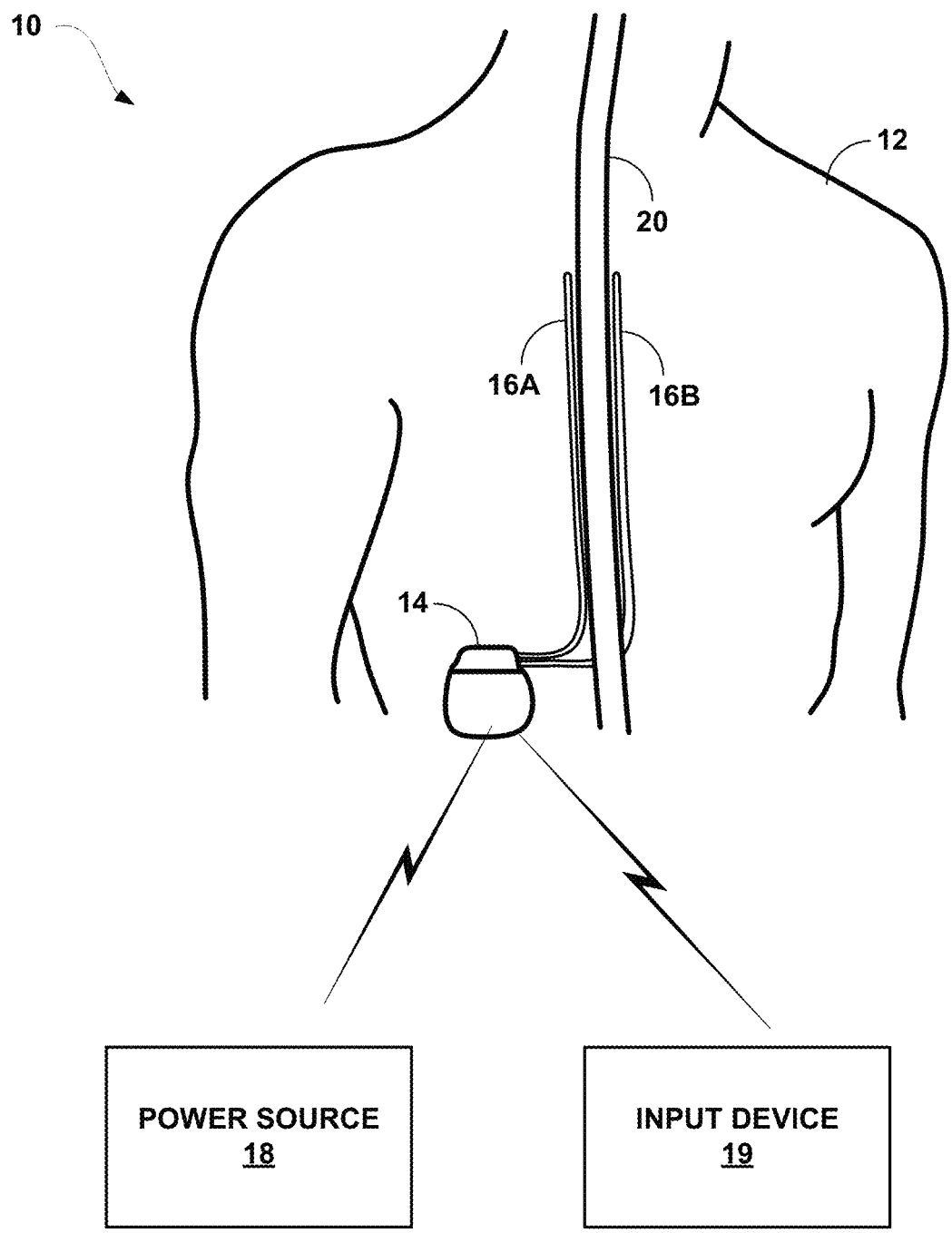
FIG. 1 is a conceptual diagram illustrating an example system that includes an input device and an implantable medical device (IMD) configured to deliver electrical stimulation therapy to a patient.

This disclosure describes example medical devices, systems, and techniques for delivering electrical stimulation therapy to treat one or more patient conditions, the electrical stimulation therapy providing a stimulation intensity significantly less than a perception or paresthesia threshold of the patient. The electrical stimulation may be a function of amplitude, frequency and pulse width of pulses within the electrical stimulation signal. The perception threshold intensity level may be the lowest determined stimulation intensity level at which a patient perception of the electrical stimulation occurs, and the paresthesia threshold intensity level may be the lowest determined stimulation intensity level at which the electrical stimulation causes paresthesia, for example, within a predetermined time range (e.g., 30 seconds) of the patient receiving the electrical stimulation.

Spinal cord stimulation (SCS) may be an effective therapy for chronic back and/or leg pain. In the last several years, dose-response studies focused on frequency settings for high dose (HD) therapies. During HD therapy, programmed amplitudes need to sustain pain relief. Most studies program amplitude according to individual patient comfort or below perception threshold. Amplitude dose-response studies have been lacking; therefore, little guidance exists regarding the minimum amplitude requirements with specific stimulation parameters. Using lower amplitude stimulation signals (e.g., or lower stimulation intensity signals, generally) would be beneficial as they are less power intensive and could extend time between battery recharges and/or battery life. Moreover, lower stimulation intensity signals may not be perceived by the patient. Therefore, the patient may have therapeutic effect without feeling the stimulation.

In some examples, HD electrical stimulation may be used according to techniques of this disclosure. With HD electrical stimulation, the high dose of electrical stimulation therapy delivers a relatively high amount of energy (e.g., electrical charge) to tissue of the patient per unit of time (e.g., one second). For example, the high dose of electrical stimulation therapy may have a charge delivery greater than about 49 microCoulobs per second and a 1.4% duty cycle. In another example, the high dose of electrical stimulation therapy may have a charge delivery greater than about 100 microCoulombs per second and a 9% duty cycle. The sufficiency of electrical stimulation in producing a desired therapeutic effect may be based on the amount of charge delivered to the tissue of the patient per unit of time. In the case of electrical stimulation pulses, the amount of charge delivered to the tissue of the patient per unit of time may be calculated by multiplying the electrical current delivered during an electrical pulse by the pulse width, which yields the amount of electrical charge delivered during a single pulse, and multiplying the amount of electrical charge delivered to the patient for one pulse by the frequency of the electrical stimulation signal. In other examples, the non-HD electrical stimulation may be used in accordance with the techniques of this disclosure.

In some examples the sub-threshold stimulation intensity electrical stimulation is delivered to a tissue site in a patient proximate to the spinal cord. In such examples, the electrical stimulation may modulate nerve fibers and produce pain relief via mechanisms that may not rely on the activation of dorsal column fibers. Although the sub-threshold electrical stimulation may or may not also activate dorsal column fibers, the electrical stimulation may not rely on activation of dorsal column fibers, which may cause paresthesia, to provide therapeutic efficacy for pain or another patient condition. However, activation of dorsal column fibers may be possible. As one non-limiting example possibility, the sub-threshold electrical stimulation may block endogenous action potentials in A-beta fibers at their branch points. A-beta fibers may be involved in some forms of chronic pain modulation, and the sub-threshold electrical stimulation may prevent A-fiber information from reaching the dorsal horn. Activation of dorsal column axons may cause paresthesia. Thus, the pain relief from the sub-threshold electrical stimulation described herein using relatively low intensity may be substantially paresthesia-free in some examples and with some patients.

It may be possible that the sub-threshold electrical stimulation described herein may modulate dural fibers, which may also be responsible for some aspects of pain (e.g., back pain) without causing activation of dorsal column fibers. The mechanisms by which the sub-threshold electrical stimulation described herein may cause pain relief may include inhibition of spinal neurons, modulation of the activity of the central nervous system (CNS) and/or brainstem, or descending inhibition (e.g., suppression of pain messages to the brain).

FIG. 1 is a conceptual diagram illustrating example system 10 that includes an implantable medical device (IMD) 14 configured to deliver electrical stimulation therapy to patient 12. In the example shown in FIG. 1, IMD 14 is configured to deliver SCS therapy. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 10 includes an IMD 14, leads 16A, 16B, power source 18, and external input device 19 shown in conjunction with a patient 12, who is ordinarily a human patient. In the example of FIG. 1, IMD 14 is an implantable electrical stimulator that is configured to generate and deliver electrical stimulation therapy to patient 12 via electrodes of leads 16A, 16B, e.g., for relief of chronic pain or other symptoms. In some examples, one of or both of the electrodes of leads 16A and 16B may be placed below the T9-10 spinal disc space and/or within 2 mm of the spine for power efficient pain relief. IMD 14 may be a chronic electrical stimulator that remains implanted within patient 12 for weeks, months, or even years. In other examples, IMD 14 may be a temporary, or trial, stimulator used to screen or evaluate the efficacy of electrical stimulation for chronic therapy.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 14 may be implanted within other suitable sites within patient 12, which may depend, for example, on the target site within patient 12 for the delivery of electrical stimulation therapy. The outer housing of IMD 14 may be configured to provide a hermetic seal for components, such as a rechargeable power source. In addition, in some examples, the outer housing of IMD 14 may be selected of a material that facilitates receiving energy to charge the rechargeable power source.

Electrical stimulation energy, which may be constant current or constant voltage based pulses (each pulse having relatively the same current or voltage), for example, is delivered from IMD 14 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at distal tips of leads 16 and/or at other positions at intermediate points along the leads. Leads 16 may be implanted and coupled to IMD 14. The electrodes may transfer electrical stimulation generated by an electrical stimulation generator in IMD 14 to tissue of patient 12. Although leads 16 may each be a single lead, leads 16 may include a lead extension or other segments that may aid in implantation or positioning of leads 16. In some other examples, IMD 14 may be a leadless stimulator with one or more arrays of electrodes arranged on a housing of the stimulator rather than leads that extend from the housing. In addition, in some other examples, system 10 may include one lead or more than two leads, each coupled to IMD 14 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of leads 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The therapy parameters (also referred to herein as a set of electrical stimulation parameter values) for a therapy program that controls delivery of stimulation therapy by IMD 14 through the electrodes of leads 16 may include information identifying which electrodes have been selected for delivery of stimulation according to a stimulation program, the polarities of the selected electrodes, i.e., the electrode configuration for the stimulation program, and voltage or current amplitude, pulse rate, and pulse width of stimulation delivered by the electrodes. Delivery of stimulation pulses will be described for purposes of illustration. However, stimulation may be delivered in other forms such as continuous waveforms. Other programs that control delivery of other therapies by IMD 14 may include other parameters, e.g., such as rate or the like in the case IMD 14 is also configured for drug delivery.

Although FIG. 1 is directed to SCS therapy, e.g., used to treat pain, in other examples system 10 may be configured to treat any other condition that may benefit from electrical stimulation therapy. For example, system 10 may be used to treat tremor, Parkinson's disease, epilepsy or sexual dysfunction), obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), peripheral nerve stimulation (PNS), peripheral nerve field stimulation (PNFS), cortical stimulation (CS), gastrointestinal stimulation, or any other stimulation therapy capable of treating a condition of patient 12.

In some examples, leads 16 may include one or more sensors configured to allow IMD 14 to monitor one or more parameters of patient 12. The one or more sensors may be provided in addition to, or in place of, therapy delivery by leads 16.

IMD 14 is configured to deliver electrical stimulation therapy (e.g., high dose, but not limited to high dose electrical stimulation therapy) to patient 12 via selected combinations of electrodes carried by one or both of leads 16, alone or in combination with an electrode carried by or defined by an outer housing of IMD 14. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent to nerves that branch off of spinal cord 20. Leads 16 may be introduced into spinal cord 20 in via any suitable region, such as the thoracic, cervical or lumbar regions. In some examples, the electrodes of leads 16 may be introduced within 2 mm of the midline of the spine in an anterior/posterior or posterior/anterior view and/or below the T9-10 spinal disc space in a lateral view. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

IMD 14 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 14 according to that program. For example, a therapy program that controls delivery of stimulation by IMD 14 in the form of pulses may define values for voltage or current pulse amplitude, pulse width, and pulse rate (frequency) for stimulation pulses delivered by IMD 14 according to that program.

Moreover, in some examples, IMD 14 delivers electrical stimulation therapy to patient 12 according to multiple therapy programs, which may be stored as a therapy program group. For example, as described below, in some examples, IMD 14 may deliver different pulses of a high duty cycle electrical stimulation signal via respective electrode combinations, and each of the electrode combinations may be associated with a respective therapy program. The therapy programs may be stored as a group, such that when IMD 14 generates and delivers electrical stimulation therapy via a selected group, IMD 14 delivers high duty cycle electrical stimulation signal via two or more therapy programs.

Moreover, "high duty cycle" (also called high dose) electrical stimulation therapy is merely one example and should not be considered limiting. The example techniques described in this disclosure may be usable with low duty cycle (also called low dose) electrical stimulation therapy.

In some examples, IMD 14 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recovery signal" or a "charge balancing signal" and may have a polarity opposite to that of the electrical stimulation signal generated and delivered by IMD 14. While recharge pulses are primarily referred to herein, in other examples, a recharge signal can have any suitable waveform.

In some examples, IMD 14 may deliver a recharge signal after delivery of multiple pulses of a high duty electrical stimulation signal, which may be defined by one therapy program or by multiple therapy programs. Thus, rather than charge balancing on a pulse-by-pulse basis (e.g., delivering one recharge pulse after each electrical stimulation pulse), in some examples, IMD 14 delivers one or more recharge pulses after delivery of two or more electrical stimulation pulses. In some examples, IMD 14 delivers a high duty electrical stimulation signal to patient 12 according to multiple therapy programs by at least interleaving pulses of two or more therapy programs, the pulses having a first polarity. In some of these examples, IMD 14 may wait to deliver one or more recharge pulses until after one or more pulses of each of the therapy programs are delivered, each recharge pulse having a second polarity opposite to the first polarity. Thus, in some examples, IMD 14 may not deliver any recharge signals between therapy programs, but, rather, may withhold the delivery of one or more recharge signals until after IMD 14 delivers a plurality of pulses according to two or more therapy programs.

In some examples, IMD 14 is configured to generate and deliver sub-threshold electrical stimulation therapy to patient 12 via two or more electrodes, e.g., of leads 16 and/or a housing of IMD 14. The amplitude, pulse width and/or frequency of the electrical stimulation signal may be selected such that a stimulation intensity level of the electrical stimulation signal is significantly less than a perception or paresthesia threshold intensity level for patient 12. The perception threshold intensity level may be the lowest determined stimulation intensity level at which a patient perception of the electrical stimulation occurs, and the paresthesia threshold intensity level may be the lowest determined stimulation intensity level at which the electrical stimulation causes paresthesia.

In some examples, IMD 14 delivers stimulation signals with an intensity of 80% or less of a patient's paresthesia or perception threshold. In other examples, IMD 14 delivers stimulation signals with an intensity of 60% or less of a patient's paresthesia or perception threshold. In other examples, IMD 14 delivers stimulation signals with an intensity of 40% or less of a patient's paresthesia or perception threshold. In other examples, IMD 14 delivers stimulation signals with an intensity of 20% or less than a patient's paresthesia or perception threshold.

In some examples, IMD 14 delivers stimulation signals with an intensity in the range of 10% to 80% of a patient's paresthesia or perception threshold. In some examples, IMD 14 delivers stimulation signals with an intensity in the range of 20% to 80% of a patient's paresthesia or perception threshold. In some examples, IMD 14 delivers stimulation signals with an intensity in the range of 20% to 60% of a patient's paresthesia or perception threshold. In some examples, IMD 14 delivers stimulation signals with an intensity in the range of 40% to 60% of a patient's paresthesia or perception threshold. In some examples, IMD 14 delivers stimulation signals with an intensity in the range of 20% to 40% of a patient's paresthesia or perception threshold. In some examples, IMD 14 delivers stimulation signals with an intensity of approximately 20% of a patient's paresthesia or perception threshold. In one example, the stimulation signal has a pulse width of about 90 microseconds and frequency of about 1000 Hz.

In some examples, IMD 14 delivers the pulses of the sub-threshold electrical stimulation signal via different electrode combinations. For example, IMD 14 may alternate delivery of pulses between two different electrode combinations, or may otherwise interleave the pulses using two or more electrode combinations in any suitable order, regardless of the number of electrode combinations with which IMD 14 delivers the pulses.

A user, such as a clinician or patient 12, may interact with a user interface of an input device 19 to program IMD 14. Programming of IMD 14 may refer generally to the generation and transfer of commands, programs, or other information to control the operation of IMD 14. In this manner, IMD 14 may receive the transferred commands and programs from input device 19 to control stimulation therapy. For example, input device 19 may transmit therapy programs, stimulation parameter adjustments, therapy program selections, therapy program group selections, user input, or other information to control the operation of IMD 14, e.g., by wireless telemetry or wired connection.

In some cases, input device 19 may be characterized as a physician or clinician programmer if it is primarily intended for use by a physician or clinician. In other cases, input device 19 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate, change or provide information relating to the stimulation therapy. For example, a patient may provide information regarding the level of pain they are feeling or regarding their level of satisfaction with the stimulation therapy. In general, a physician or clinician programmer may support selection and generation of programs by a physician or clinician for use by IMD 14, whereas a patient programmer may support adjustment and selection of such programs by a patient during ordinary use. In other examples, input device 19 may be included, or part of, an external charging device or power source, such as power source 18, that recharges a power source of IMD 14. In this manner, a user may program and charge IMD 14 using one device, or multiple devices.

As described herein, information may be transmitted between input device 19 and IMD 14. Therefore, IMD 14 and input device 19 may communicate via wireless communication using any techniques known in the art. Examples of communication techniques may include, for example, radiofrequency (RF) telemetry and inductive coupling, but other techniques are also contemplated. In some examples, input device 19 may include a communication head that may be placed proximate to the patient's body near the IMD 14 implant site in order to improve the quality or security of communication between IMD 14 and input device 19. In some examples, input device 19 and power source 18 are housed within a single housing. Communication between input device 19 and IMD 14 may occur during power transmission or separate from power transmission.

Although IMD 14 is generally described herein, techniques of this disclosure may also be applicable to external or partially external medical devices in other examples. For example, IMD 14 may instead be configured as an external medical device coupled to one or more percutaneous medical leads. The external medical device may be a chronic, temporary, or trial electrical stimulator. In addition, an external electrical stimulator may be used in addition to one or more IMDs 14 to deliver electrical stimulation described herein.

In accordance with one or more examples described in this disclosure, IMD 14 may be configured to deliver electrical stimulation therapy with electrical stimulation signals having sub-threshold (e.g., sub-paresthesia or sub-perception) intensity. For instance, patient 12 may not perceive the electrical stimulation (e.g., no paresthesia) but would experience therapeutic effect. The intensity of the electrical stimulation signal may be substantially lower than the intensity of the electrical stimulation signal at the perception or paresthesia threshold intensity.

As one example, the intensity of the sub-threshold electrical stimulation signal may be 80% or less of the intensity of the perception or paresthesia threshold intensity. As another example, the intensity of the sub-threshold electrical stimulation signal may be 60% or less of the intensity of the perception or paresthesia threshold intensity. As another example, the intensity of the sub-threshold electrical stimulation signal may be 40% or less of the intensity of the perception or paresthesia threshold intensity. As another example, the intensity of the sub-threshold electrical stimulation signal may be 20% or less of the intensity of the perception or paresthesia threshold intensity.

In some examples, IMD 14 delivers stimulation signals with an intensity in the range of 10% to 80% of a patient's paresthesia or perception threshold. In some examples, IMD 14 delivers stimulation signals with an intensity in the range of 20% to 80% of a patient's paresthesia or perception threshold. In some examples, IMD 14 delivers stimulation signals with an intensity in the range of 20% to 60% of a patient's paresthesia or perception threshold. In some examples, IMD 14 delivers stimulation signals with an intensity in the range of 40% to 60% of a patient's paresthesia or perception threshold. In some examples, IMD 14 delivers stimulation signals with an intensity in the range of 20% to 40% of a patient's paresthesia or perception threshold.

There may be a variety of waveforms of the sub-threshold electrical stimulation signals. As one example, the pulse width of the sub-threshold electrical stimulation signal may be 90 micro-seconds and the frequency may be 1000 Hz. The amplitude may be 20% of the amplitude at which patient perceived the stimulation or experienced paresthesia. For instance, IMD 14 (e.g., automatically or in response to instructions from the clinician or patient 12) may start with stimulation having 90 micro-seconds pulse width and frequency of 1000 Hz, and titrate the amplitude upwards until patient 12 perceives the stimulation (e.g., arrives at the perception amplitude). As used herein, titration may involve either or both of: 1) changing the intensity (e.g., amplitude) of an electrical stimulation signal in a continuous manner such that stimulation is delivered to patient 12 during titration as the electrical stimulation signal is "ramped-up" or "ramped-down"; or 2) changing the intensity (e.g., amplitude) of an electrical stimulation signal in a discontinuous manner such that stimulation is delivered to patient 12 at one intensity level and then delivered to patient 12 at another intensity level without a "ramp-up" or "ramp-down", such as in a step function. In the second case, there may or may not be a period or time during which no stimulation is being delivered to patient 12. In some examples, IMD 14 (e.g., automatically or in response to instructions from the clinician or patient 12) may reduce the amplitude to some fraction (e.g., in range of 80% to 10%, including 80% or less, 60% or less, 40% or less, or 20% or less) of the amplitude found from the titrating. As used herein, "automatically" means without user intervention or control. In some examples, the IMD 14 may then deliver therapy at the reduced amplitude. In other examples, IMD 14 (e.g., automatically or in response to instructions from the clinician or patient 12) may change the amplitude in a different order that is not consecutively higher or consecutively lower. For example, IMD 14 may deliver stimulation at an amplitude that is 60%, then 20%, then 80%, the 40% of patient 12's paresthesia threshold or perception threshold.

In this manner, IMD 14 may be configured to generate a lower intensity electrical stimulation signal comprising a plurality of pulses. For instance, the lower intensity electrical stimulation signal has a stimulation intensity that is significantly lower than a paresthesia or perception threshold of the patient. IMD 14 may deliver the lower intensity electrical stimulation signal to the patient. As described, delivery of such lower intensity electrical stimulation signal extends the operational life of IMD 14 and results in efficacious treatment with minimal impact on the quality of life of patient 12.

There may be various ways in which IMD 14 generates the lower intensity electrical stimulation signal. For instance, IMD 14 (e.g., automatically or based on input from a clinician or patient 12) may titrate the intensity down, starting from the paresthesia or perception threshold, to a first intensity. If patient 12 experiences no pain, IMD 14 may further titrate the intensity down to a second intensity, and so forth until IMD 14 reaches a lower intensity electrical stimulation (e.g., lowest electrical stimulation signal where there is therapeutic result that is below perception or paresthesia threshold).

In some examples, after titrating the intensity down, patient 12 may indicate discomfort, unsatisfaction, or pain. In some cases, even under such circumstances, IMD 14 may further titrate the intensity down. After further downward titration in the intensity, patient 12 may again experience therapeutic results.

The reduction in the intensity may be based on a set scale of reduction (e.g., 80%, then 60%, then 40%, and then 20%). For example, some patients may need to receive stimulation at 80% of their paresthesia threshold or perception threshold prior to receiving stimulation at a lower intensity in order for the lower intensity stimulation to be effective. In some examples, the reduction in intensity may be relatively random (e.g., 80%, then 40%, then 60%, and then 20%, or some other permutation). For example, some patients may become accustom to a setting or a predictable change in settings over time. By reducing the intensity of the stimulation signal in a more random manner, treatment may be more effective to those patients.

Figure 2:
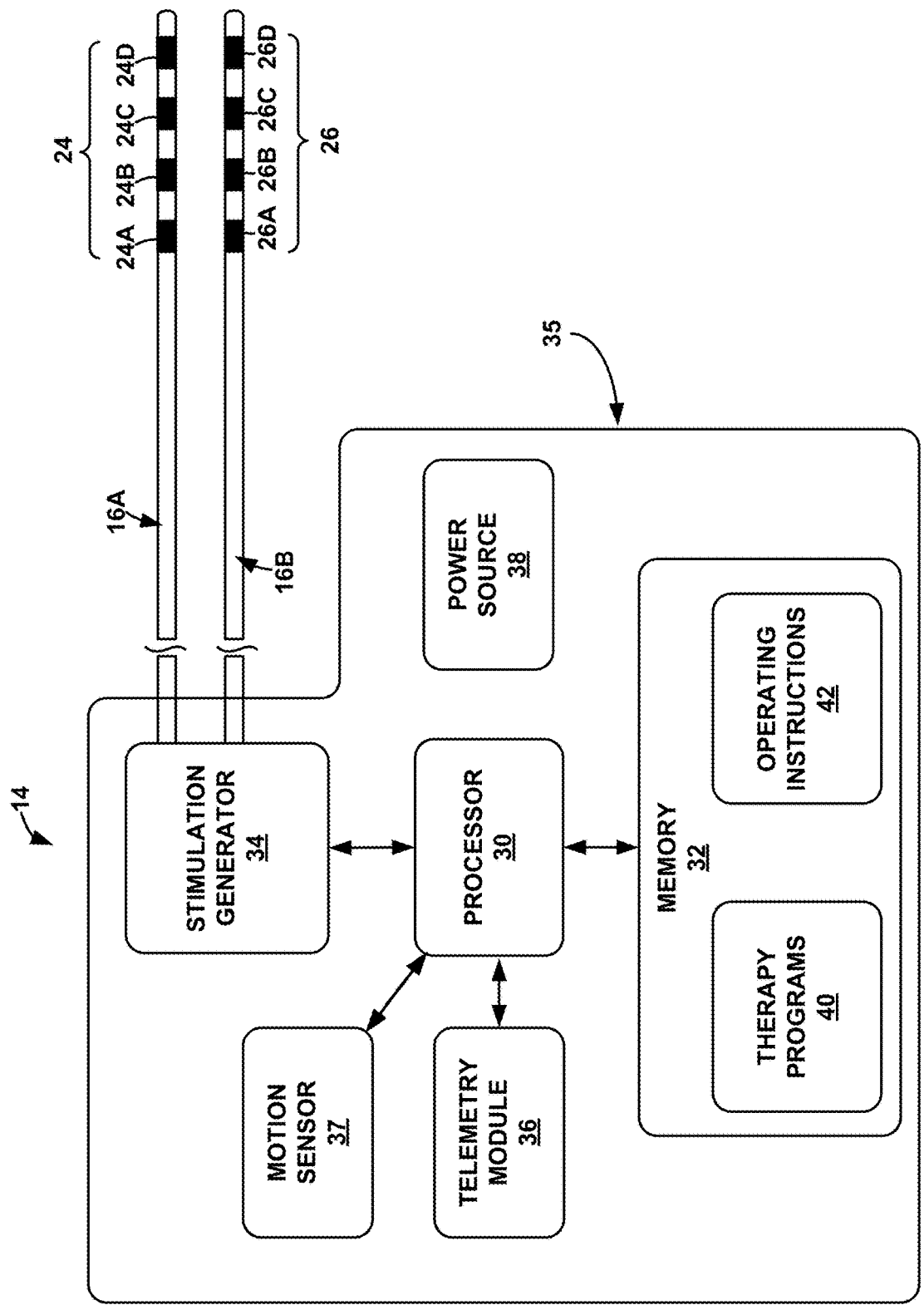
FIG. 2 is a block diagram of the example IMD of FIG. 1.

FIG. 2 is a functional block diagram illustrating various components of an example IMD 14. In the example shown in FIG. 2, IMD 14 includes processor 30, memory 32, stimulation generator 34, telemetry module 36, and power source 38. In other examples, IMD 14 may include a greater or fewer number of components. For example, IMD 14 may also include a sensing module configured to sense one or more patient parameters, an inductive coil to receive power from an external charging device (such as power source 18 of FIG. 1), and a recharge module that manages recharging of power source 38.

Processor 30 is operably connected to and configured to access information from memory 32 and to control stimulation generator 34 and telemetry module 36. Components described as processor 30 and other processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more DSPs, ASICs, FPGAs, programmable logic circuitry, or the like, either alone or in any suitable combination.

Memory 32 may store therapy programs 40 (or other instructions that specify therapy parameter values for the therapy provided by stimulation generator 34 and IMD 14), operating instructions 42 for execution by processor 30, and any other information regarding therapy of patient 12. In some examples, memory 32 may also store instructions for communication between IMD 14 and input device 19, or any other instructions required to perform tasks attributed to IMD 14. Memory 32 may include separate memories for storing therapy programs, operating instructions, and any other data that may benefit from separate physical memory modules.

Memory 32 may comprise any suitable storage media, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Although processor 30, stimulation generator 34, and telemetry module 36 are described as separate modules, in some examples, processor 30, stimulation generator 34, and telemetry module 36 may be functionally integrated. In some examples, processor 30, stimulation generator 34, and telemetry module 36 may correspond to individual hardware units, such as ASICs, DSPs, FPGAs, or other hardware units.

Stimulation generator 34 forms a therapy delivery module of IMD 14. Processor 30 controls stimulation generator 34 to generate and deliver electrical stimulation via electrode combinations formed by a selected subset of electrodes 24A-24D, 26A-26D (collectively, "electrodes 24, 26") of leads 16. Stimulation generator 34 may deliver electrical stimulation therapy via electrodes on one or more leads 16, e.g., as stimulation pulses. Stimulation generator 34 may include stimulation generation circuitry to generate stimulation pulses and, in some examples, switching circuitry to switch the stimulation across different electrode combinations, e.g., in response to control by processor 30. In other examples, stimulation generator 34 may include multiple current sources to drive more than one electrode combination at one time.

In some examples, processor 30 controls stimulation generator 34 by accessing memory 32 to selectively access and load at least one of the therapy programs 40 to stimulation generator 34. The stimulation parameter values of the stored therapy programs 40 may include, for example, a voltage amplitude, a current amplitude, a pulse frequency, a pulse width, a duty cycle, and a subset of electrodes 24, 26 of leads 16 for delivering the electrical stimulation signal. An electrode configuration may include the one or more electrodes 24, 26 with which stimulation generator 34 delivers the electrical stimulation to tissue of a patient, and the associated electrode polarities.

In some examples, IMD 14 may deliver a sub-threshold electrical stimulation signal to a target tissue site within patient 12 via one electrode combination, such that all pulses are delivered via the same electrode combination. In other examples, IMD 14 may deliver a sub-threshold electrical stimulation signal to a target tissue site within patient 12 via two or more electrode combinations, such that IMD 14 delivers at least two different pulses of a sub-threshold electrical stimulation signal via respective electrode combinations. The delivery of different pulses via respective electrode combinations may help target the electrical stimulation to a target tissue site (e.g., in the case of pain relief, the target may be within 2 mm of a midline of spinal cord 20, for example, and below the T9-T10 spinal disc space). The electrical stimulation delivered by each electrode combination, which may be referred to as a sub-signal, may be interleaved (e.g., delivered at different times) to define the sub-threshold electrical stimulation signal. In some of these examples, each sub-signal is associated with a respective therapy program. Thus, processor 30 may control stimulation generator 34 to generate and deliver a sub-threshold electrical stimulation signal by at least accessing memory 32 to selectively access and load multiple therapy programs 40 to stimulation generator 34.

IMD 14 also includes components to receive power from input device 19 or a separate charging device, such as power source 18, to recharge a battery of power source 38. Power source 38 may include one or more capacitors, batteries, or other energy storage devices. IMD 14 may thus also include an inductive coil and a recharge module (both not shown) configured to manage the recharging session for power source 38. Although inductive coupling may be used to recharge power source 38, other wireless energy transfer techniques may alternatively be used. Alternatively, power source 38 may not be rechargeable.

Processor 30 may also control the exchange of information with input device 19 and/or an external programmer using telemetry module 36. Telemetry module 36 may be configured for wireless communication using RF protocols, inductive communication protocols, or any other suitable technique. To support the wireless communication, telemetry module 36 may include appropriate electronic components, such as amplifiers, filters, mixers, encoders, decoders, and the like. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36.

In some examples, stimulation generator 34 may generate a lower intensity electrical stimulation signal comprising a plurality of pulses with a stimulation intensity that is significantly lower than a paresthesia or perception threshold of a patient and deliver the lower intensity electrical stimulation signal to the patient through electrode 24 and/or 26. In some examples, IMD 14 delivers stimulation signals with an intensity in the range of 10% to 80% of a patient's paresthesia or perception threshold. In some examples, IMD 14 delivers stimulation signals with an intensity in the range of 20% to 80% of a patient's paresthesia or perception threshold. In some examples, IMD 14 delivers stimulation signals with an intensity in the range of 20% to 60% of a patient's paresthesia or perception threshold. In some examples, IMD 14 delivers stimulation signals with an intensity in the range of 40% to 60% of a patient's paresthesia or perception threshold. In some examples, IMD 14 delivers stimulation signals with an intensity in the range of 20% to 40% of a patient's paresthesia or perception threshold. In some examples, IMD 14 delivers stimulation signals with an intensity of approximately 20% of a patient's paresthesia or perception threshold. In one example, the stimulation signal has a pulse width of about 90 microseconds and frequency of about 1000 Hz.

Figure 3:
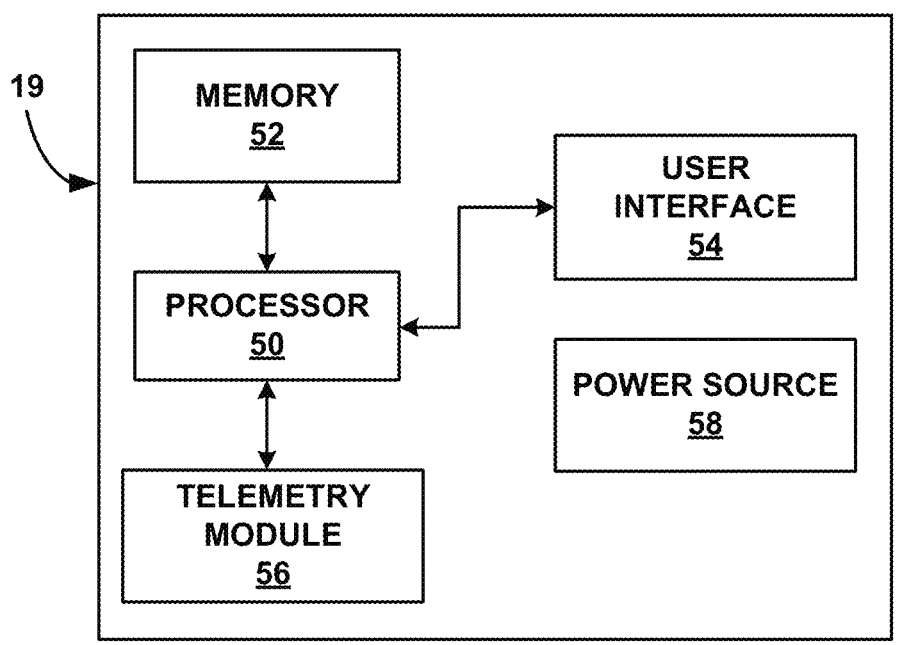
FIG. 3 is a block diagram of the example input device of FIG. 1.

FIG. 3 is a block diagram of an example input device 19. While input device 19 may generally be described as a hand-held device, input device 19 may be a larger portable device or a more stationary device in some examples. In addition, in other examples, input device 19 may be included as part of an external charging device or include the functionality of an external charging device, such as power source 18. As illustrated in FIG. 3, input device 19 may include a processor 50, memory 52, user interface 54, telemetry module 56, and power source 58. Memory 52 may store instructions that, when executed by processor 50, cause processor 50 and input device 19 to provide the functionality ascribed to input device 19 throughout this disclosure.

Input device 19 comprises any suitable arrangement of hardware, alone or in combination with software and/or firmware, to perform the techniques attributed to input device 19, and processor 50, user interface 54, and telemetry module 56 of input device 19. In various examples, processor 50 may include one or more processors, such as one or more microprocessors, DSPs, ASICs, FPGAs, or any other equivalent integrated or discrete logic circuitry, as well as any combinations of such components. Input device 19 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 correspond to individual hardware units, such as ASICs, DSPs, FPGAs, or other hardware units.

Memory 52 may store instructions that, when executed by processor 50, cause processor 50 and input device 19 to provide the functionality ascribed to input device 19 throughout this disclosure. In addition, in some examples, memory 52 stores one or more therapy programs for execution by IMD 14 to deliver high dose electrical stimulation therapy.

User interface 54 may include a button or keypad, lights, a speaker and microphone for voice commands, a display, such as a liquid crystal (LCD), light-emitting diode (LED), or organic light-emitting diode (OLED). In some examples the display may be a touch screen. User interface 54 may be configured to display any information related to the delivery of stimulation therapy, such as currently selected parameter values, intensity thresholds, or any other therapy information. User interface 54 may also receive user input via user interface 54. The input may be, for example, in the form of pressing a button on a keypad or selecting an icon from a touch screen. The input may request starting or stopping electrical stimulation, or requesting some other change to the delivery of electrical stimulation. Additionally, the input may provide information about how the patient is feeling about the treatment, such their level of satisfaction with the treatment. The level of satisfaction may be determined by the level of pain they are feeling or by their answers to questions such as are they feeling the treatment, are they feeling the treatment all the time or just some of the time, and if they are uncomfortable.

Telemetry module 56 may support wireless communication between IMD 14 and input device 19 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between input device 19 and IMD 14 include RF communication according to the 802.11 or Bluetooth specification sets or other standard or proprietary telemetry protocols. In this manner, other external devices may be capable of communicating with input device 19 without needing to establish a secure wireless connection.

FIG. 4 is a timing diagram of an example electrical stimulation signal 60 that IMD 14 may generate and deliver to patient 12. Electrical stimulation signal 60 includes a plurality of pulses 62A-62G (collectively, "pulses 62"). Although seven pulses are shown in FIG. 4, electrical stimulation signal 60 may include any number of pulses, which may depend on the time period over which IMD 14 delivers electrical stimulation signal 60 to patient 12. Each pulse 62 has an amplitude $AMP_A$ and a pulse width $PW_A$. In some examples, each pulse 62 of electrical stimulation signal 60 can have the same amplitude $AMP_A$ and pulse width $PW_A$. In other examples, at least one pulse 62 of electrical stimulation signal 60 may have a different amplitude $AMP_A$ and/or pulse width $PW_A$ than another pulse 62.

Stimulation generator 34 of IMD 14 may generate and deliver a sub-threshold electrical stimulation signal 60 using any suitable technique. In some examples, stimulation generator 34 may deliver each of the pulses 62 with the same electrode combination. In some examples, stimulation generator 34 may deliver one or more recharge pulses (also referred to as a "recovery pulse" or a "charge balancing pulse") after a predetermined number of pulses 62 are delivered, the predetermined number being greater than one. Thus, rather than charge balancing on a pulse-by-pulse basis (e.g., delivering one recharge pulse after each pulse 62), in some examples, processor 30 may control stimulation generator 34 to deliver one or more recharge pulses after delivery of two or more pulses 62. In other examples, processor 30 may control stimulation generator 34 to deliver pulses to promote charge balance on a pulse-by-pulse basis.

In other examples, stimulation generator 34 may deliver different pulses 62 via respective electrode combinations, such that the sub-threshold electrical stimulation signal is delivered via multiple therapy programs. For example, under the control of processor 30, stimulation generator 34 may deliver pulses 62A, 62C, 62E, 62G with a first electrode combination, and deliver pulses 62B, 62D, 62F with a second, different electrode combination. In this example, pulses 62A, 62C, 62E, 62G can be part of a first sub-signal delivered via the first electrode combination, and pulses 62B, 62D, 62F can be part of a second sub-signal delivered via the second electrode combination. The first and second sub-signals, when delivered together over time such that the pulses of the sub-signals interleaved together as shown in FIG. 4, combine to define sub-threshold electrical stimulation signal 60. Although two sub-signals are used here as an example, in other examples, stimulation generator 34 of IMD 14 may generate and deliver sub-threshold cycle electrical stimulation signal 60 using any suitable number of sub-signals. In some examples, stimulation generator 34 may generate each sub-signal using a respective therapy program, which may be stored as a group in memory 32 of IMD 14 (FIG. 2).

In some examples in which stimulation generator 34 may deliver different pulses 62 via different electrode combinations, processor 30 may control stimulation generator 34 may deliver one or more recharge pulses after a predetermined number of pulses 62 are delivered, the predetermined number being greater than one. The predetermined number of pulses 62 may include pulses generated according to different therapy programs. Thus, in some examples, stimulation generator 34 may deliver one or more recharge pulses after pulses of different sub-signals are delivered. For example, under the control of processor 30, stimulation generator 34 may deliver one or more recharge pulses after stimulation generator delivers pulses 62A and 62B, rather than delivering one or more recharge pulses between pulses 62A, 62B, and then again after pulse 62B. In this example, stimulation generator 34 may wait to deliver one or more recharge pulses until after stimulation generator delivers pulses 62C and 62D, rather than delivering one or more recharge pulses between pulses 62C, 62D, and then again after pulse 62B. In other examples, processor 30 may control stimulation generator 34 to deliver recharge pulses to balance charge on a pulse-by-pulse basis.

Stimulation generator 34 can deliver the sub-signals using electrodes from a single lead 16A or from two or more leads 16B. For example, under the control of processor 30, stimulation generator 34 may deliver a first pulse 62A with electrode 24A of lead 16A together with a housing electrode of outer housing 35 of IMD 14 and deliver pulse 62B with electrode 24B of lead 16A together with a housing electrode of outer housing 35. As another example, under the control of processor 30, stimulation generator 34 may deliver a first pulse 62A with electrodes 24A, 24B of lead 16A and deliver pulse 62B with electrodes 24B, 24C of the same lead 16A. In another example, stimulation generator 34 may deliver different pulses 62 with electrodes of different leads. Processor 30 may, for example, control stimulation generator 34 to alternate delivery of pulses 62 between leads 16A, 16B, or control stimulation generator 34 to otherwise deliver pulses 62 with electrodes of each lead 16A, 16B at different times. For example, under the control of processor 30, stimulation generator 34 may deliver a first pulse 62A with electrodes 24A, 24B of lead 16A and deliver pulse 62B with electrodes 26A, 26B of lead 16B.

Regardless of the number of electrode combinations with which stimulation generator 34 delivers pulses 62, the combination of pulses 62 may combine to define electrical stimulation signal 60 having a sub-threshold intensity level as described herein.

Delivery of each sub-signal by stimulation generator 34 may generate a stimulation field within tissue of the patient, where the stimulation field may be a volume of tissue through which the electrical current from the delivered sub-signal propagates. The electrode combinations with which pulses 62 are delivered and the frequency of sub-threshold electrical stimulation signal 60 can be selected such that the combination of pulses 62A, 62B (or any other number of pulses 62 delivered from any suitable number of different electrode combinations) results in stimulation fields that overlap. The region of overlap of the stimulation fields may be configured to target neural areas responsive to the sub-threshold mechanisms described herein, e.g., to provide the desired therapeutic effect. In some examples, the regions of the stimulation fields that do not overlap may not provide any therapeutic effect.

In some examples, processor 30 controls stimulation generator 34 to generate and deliver pulses 62 via two or more therapy programs, each defining a respective electrode combination. For example, some pulses 62 may be part of a first sub-signal defined by a first therapy program and delivered by stimulation generator 34 via a first electrode combination, and other pulses 62 may be part of a second sub-signal defined by a second therapy program and delivered by stimulation generator 34 via a second electrode combination. Stimulation generator 34 may interleave delivery of pulses of the first and second sub-signals, such that the pulses only partially overlap in time or do not overlap in time. Delivery of the first and second sub-signals may generate respective stimulation fields within tissue. In some examples, the stimulation fields, individually and when overlapping, have stimulation intensities less than at least one of: a perception threshold or a paresthesia threshold of the patient. In some examples, processor 30 controls stimulation generator 34 to deliver a recharge signal following the delivery of at least one pulse of each of the first and second electrical sub-signals.

Delivering electrical stimulation signal 60 as multiple sub-signals delivered via respective electrode combinations may help reduce the charge density at the electrode-tissue interface of particular electrodes. In addition, delivering electrical stimulation signal 60 via multiple sub-signals may provide more flexibility in programming the electrical stimulation therapy that has an intensity below the perception or paresthesia threshold intensity level of patient 12 because the sub-signals may each have relatively low stimulation intensities, but due to the overlap in the stimulation fields that may result from the interleaving of the delivery of the sub-signals, the sub-signals may be combined to provide efficacious electrical stimulation therapy to patient 12.

Stimulation generator 34 may recharge at the end of the pulse train, e.g., after the pulses of the plurality of sub-signals are delivered. In other examples, stimulation generator 34 may recharge after each delivered pulse.

FIG. 5 is a timing diagram of another example electrical stimulation signal 64 that IMD 14 may generate and deliver to patient 12. Electrical stimulation signal 64 includes a plurality of pulses 66. Stimulation signal 64 may include any number of pulses 66, which may depend on the duration that IMD 14 delivers stimulation signal 64 to patient 12. In contrast to electrical stimulation signal 60, each pulse 66 of electrical stimulation signal 64 has a smaller pulse width $PW_B$ and a higher amplitude $AMP_B$ than each of the pulses 62 of electrical stimulation signal 60. The charge density of electrical stimulation signal 64 may be similar to (e.g., identical or nearly identical) to electrical stimulation signal 60, e.g., because the higher amplitude $AMP_B$ may compensate for the decrease in energy delivery resulting from the decrease in pulse width $PW_B$ relative to pulses 62 of electrical stimulation signal 60. As with amplitude $AMP_A$, amplitude $AMP_B$ may be less than the paresthesia or perception threshold of patient 12. In addition, the duty cycle of electrical stimulation signal 64 can be substantially the same as the duty cycle of electrical stimulation signal 60 (FIG. 4), despite the smaller pulse width $PW_B$, due at least in part to the greater number of pulses 66 per second than electrical stimulation signal 60.

Stimulation generator 34 of IMD 14 may generate and deliver high duty cycle electrical stimulation signal 64 using any suitable technique, such as those described with respect to electrical stimulation signal 60. In some examples, stimulation generator 34 of IMD 14 may also generate and deliver recharge pulses as discussed above with respect to FIG. 4.

FIG. 6 is a timing diagram of an example burst electrical stimulation signal 68, which includes a plurality of pulses 70A-70H (collectively, "pulses 70"). Burst electrical stimulation signal 68 has fewer pulses 70 per unit of time (e.g., one second) than the electrical stimulation signals 60, 64 (FIGS. 4 and 5). During a particular period of time, e.g., one second as shown in FIG. 6, an IMD delivers a burst of pulses 70A-70D of burst electrical stimulation signal 68 for a first time period 72, which is immediately followed by a second period of time 74 during which the IMD does not deliver any electrical stimulation, but, rather, delivers one or more recovery pulses. Second time period 74 may be referred to as a "recovery period." After second time period 74, the IMD 14 may deliver another burst of pulses 70E-70H, which may be followed by another recovery period. First and second time periods 72, 74 may be substantially equal (e.g., equal or nearly equal) in some examples, and different in other examples. In some examples, stimulation generator 34 of IMD 14 may also generate and deliver recharge pulses as discussed above with respect to FIG. 4.

In contrast to burst electrical stimulation signal 68, delivery of electrical stimulation signals 60, 64 by IMD 14 may provide better targeting of target tissue sites. For a given dose, burst electrical stimulation signal 68 may result in activation of more neural tissue (e.g., a larger volume of tissue) than electrical stimulation signals 60, 64.

FIG. 7 is a timing diagram of an example high frequency electrical stimulation signal 76, which includes a plurality of pulses 78. High frequency electrical stimulation signal 76 has a higher frequency than electrical stimulation signals 60, 64 (FIGS. 4 and 5, such that high frequency electrical stimulation signal 76 has a greater number of pulses 78 per unit of time than high duty cycle electrical stimulation signals 60, 64). For example, stimulation generator 34 of IMD 14 may generate high frequency electrical stimulation signal 76 with a frequency of 1500 Hz to about 100 kiloHz, or greater, whereas high duty cycle electrical stimulation signals 60, 64 may each have a frequency less than or equal to about 1400 Hz. In some examples, stimulation generator 34 of IMD 14 may also generate and deliver recharge pulses as discussed above with respect to FIG. 4.

For a given duty cycle, high frequency electrical stimulation signal 76 may result in activation of more neural tissue than electrical stimulation signals 60, 64, which have pulses 62, 66, respectively, with higher pulse widths than pulses 78 of high frequency electrical stimulation signal 76. The lower frequency of electrical stimulation signals 60, 64 may allow for a larger therapeutic window for the pulse amplitudes $AMP_A$ and $AMP_A$, which may help a clinician tailor the electrical stimulation to a particular patient to allow for different neural mechanisms to be activated in order to elicit a therapeutic response from the patient. The therapeutic window for the pulse amplitudes $AMP_A$ and $AMP_A$ can be, for example, the range of amplitude values that provide efficacious therapy to patient 12 without resulting in undesired side effects.

Figure 8A:
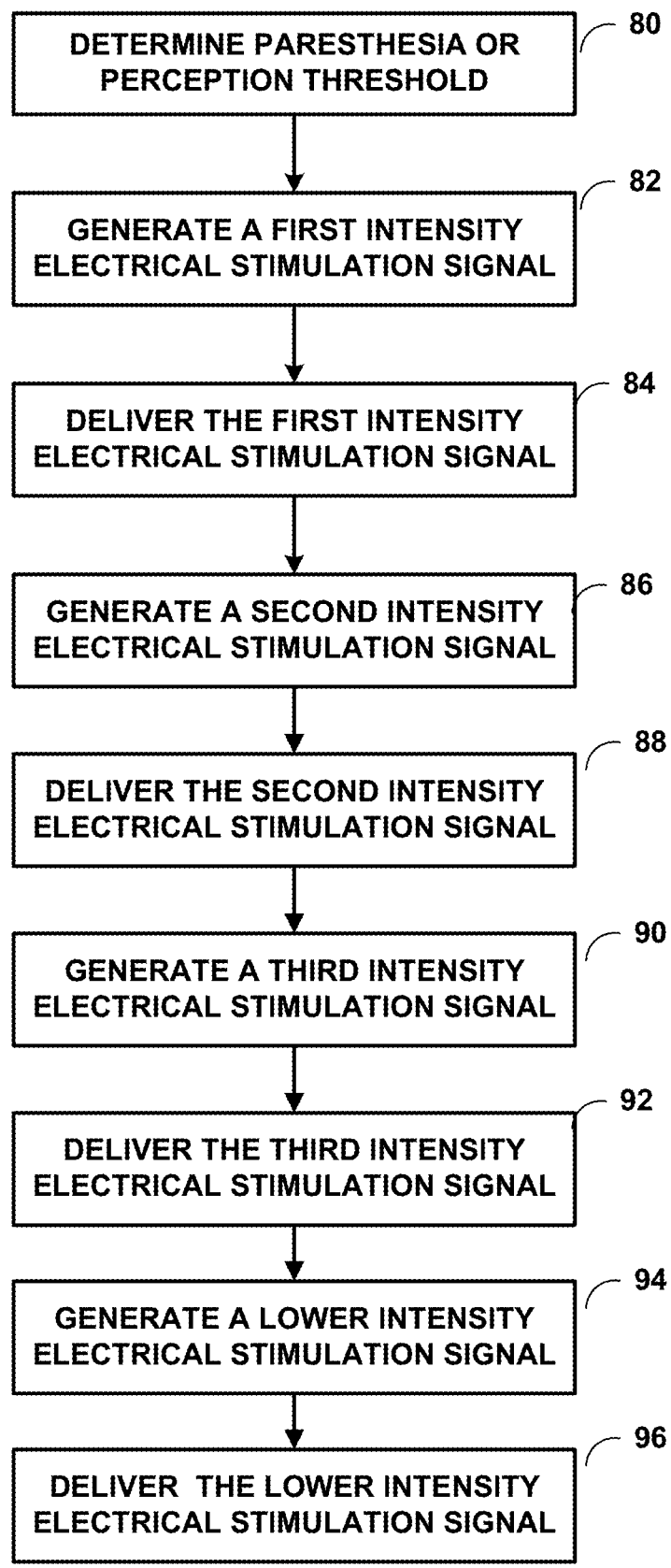
FIGS. 8A-8E are flow diagrams of example methods according to techniques of this disclosure.

The electrical stimulation parameter values with which IMD 14 may generate and deliver the sub-threshold electrical stimulation described herein may be selected using any suitable technique. FIG. 8A is a flow diagram of an example technique for titrating to select the electrical stimulation parameter values. While FIG. 8A is described with respect to processor 30 of IMD 14, in other examples, processor 50 of input device 19 may perform any part of the technique described with respect to FIG. 8A, alone or in combination with processor 30 of IMD 14. Also, while FIG. 8A is described with a certain number of titrations, any number may be used. In some examples, the technique of FIG. 8A may be utilized to attempt to titrate to an ideal intensity electrical stimulation signal for a given patient, for example, patient 12.

In the technique shown in FIG. 8A, processor 30 determines a paresthesia or perception threshold intensity level for patient 12 (80), e.g., using the technique described below with respect to FIG. 8B, by retrieving a stored paresthesia or perception threshold intensity level from memory 32 (FIG. 2), or by receiving a paresthesia or perception threshold intensity level from another device, e.g., input device 19, from for example a physician or clinician. Processor 30 may, for example, determine the paresthesia threshold, determine the perception threshold, determine the lower of the paresthesia threshold intensity level or the perception threshold intensity level for patient 12, or determine the higher of the paresthesia threshold intensity level or the perception threshold intensity level for patient 12 (80).

A paresthesia threshold intensity level may be a lowest determined electrical stimulation intensity level at which patient 12 first perceives paresthesia from the electrical stimulation delivered by IMD 14. A perception threshold intensity level may be a lowest determined electrical stimulation intensity level at which patient 12 first perceives the electrical stimulation delivered by IMD 14. In some cases, depending on the patient and/or the target electrical stimulation site within the patient, the patient may first perceive the electrical stimulation delivered by IMD 14 as paresthesia. Thus, in some cases, the perception threshold intensity level may be substantially the same (e.g., identical or nearly identical) as the paresthesia threshold intensity level. In other cases, however, a patient may first perceive the electrical stimulation as a sensation different than paresthesia. Thus, in some cases, the perception threshold intensity level may be different than the paresthesia threshold intensity level. In these examples, a clinician may program IMD 14 and/or input device 19 to use either the perception or paresthesia threshold intensity levels to select the electrical stimulation parameter with the technique shown in FIG. 8A.

After determining one or both of the paresthesia threshold intensity level or the perception threshold intensity level, processor 30 may control stimulation generator 34 to generate a first intensity electrical stimulation signal (82). The first intensity electrical stimulation signal may be a subthreshold electrical stimulation signal. IMD 14 then may deliver the first intensity electrical stimulation signal to the patient 12 through one or more of the electrodes 24 and 26 (84).

In some examples, processor 30 scales one or more of the amplitude, pulse width or frequency from the electrical stimulation signal used to determine the paresthesia threshold or perception threshold to generate parameters for the first intensity electrical stimulation signal. In some examples, processor 30 may utilize a strength-duration curve to determine these parameters. An example of a strength duration curve is an amplitude-pulse width curve. The amplitude-pulse width curve may reflect, for a selected stimulation frequency, different combinations of amplitude and pulse width values that contribute to a stimulation field in a substantially similar manner. For example, the amplitude-pulse width curve may indicate that a first electrical stimulation signal with a first amplitude and a first pulse width, and a second electrical stimulation signal having a higher amplitude pulse with a shorter pulse width (i.e., shorter than the first pulse width) may both provide electrical stimulation therapy below the paresthesia or perception threshold of patient 12. Each position on the amplitude-pulse width curve, or each position within a particular range of positions along the amplitude-pulse width curve, may result in a substantially similar stimulation energy when the other therapy parameter values, such as a frequency, remain substantially constant (e.g., the other therapy parameter values may remain within a particular range of therapy parameter values, such as within a 10% window or less from the values defined by the therapy program). Thus, for a given stimulation frequency, the amplitude-pulse width curve may define, e.g., via the amplitude-pulse width combinations associated with the area under the curve and/or along the curve, the amplitude and pulse width combinations that provide electrical stimulation therapy having an intensity level below the paresthesia or perception threshold intensity level of patient 12.

After a first period of time, processor 30 may control stimulation generator 34 to generate a second intensity electrical stimulation signal (86) that is different than the first intensity electrical stimulation signal. In some examples, the second intensity electrical stimulation signal is less intensive than the first intensity electrical stimulation signal. In other examples, the second intensity electrical stimulation signal is more intensive than the first intensity electrical stimulation signal. IMD 14 then may deliver the second intensity electrical stimulation signal to the patient 12 through one or more of the electrodes 24 and 26 (88).

In some examples, processor 30 scales one or more of the amplitude, pulse width and frequency from the first intensity electrical stimulation signal to generate parameters for the second intensity electrical stimulation signal. In some examples, processor 30 may utilize a strength-duration curve (e.g., as described above) to determine these parameters.

After a second period of time, which may be the same as the first period of time or different than the first period of time, processor 30 may control stimulation generator 34 to generate a third intensity electrical stimulation signal (90). The third intensity electrical stimulation signal may be different than the first intensity electrical signal and the second intensity electrical signal. The IMD 14 then may deliver the third intensity electrical stimulation signal to the patient 12 through one or more of the electrodes 24 and 26 (92).

In some examples, processor 30 scales one or more of the amplitude, pulse width and frequency from the second intensity electrical stimulation signal to generate parameters for the third intensity electrical stimulation signal. In some examples, processor 30 may utilize a strength-duration curve (e.g., as described above) to determine these parameters.

After a third period of time, which may be the same as the first or the second period of time or which may be different than both the first and the second period of time, processor 30 may control stimulation generator 34 to generate a lower intensity electrical stimulation signal (94). The lower intensity electrical stimulation signal may be different than the first, second and third intensity electrical stimulation signals. IMD 14 then may deliver the lower intensity electrical stimulation signal to the patient 12 through one or more of the electrodes 24 and 26 (96).

In some examples, processor 30 scales one or more of the amplitude, pulse width and frequency from the third intensity electrical stimulation signal to generate parameters for the lower intensity electrical stimulation signal. In some examples, processor 30 may utilize a strength-duration curve (e.g., as described above) to determine these parameters.

In one example, each of the electrical stimulation signals delivered to the patient (84) (88) (92) (96) are sub-threshold signals. In another example, each of the electrical stimulation signals delivered to the patient (84) (88) (92) (96) are progressively less intensive. In yet another example, each of the electrical stimulation signals delivered to the patient (84) (88) (92) (96) are not progressively less intensive. For example, some patients may adapt to predictable changes in intensity and the treatment may lose efficacy. By delivering the electrical stimulation signals to the patient in a non-progressively less intensive manner, efficacy may be improved. In addition, by delivering electrical stimulation signals in a non-progressively less intensive manner, may help lower overall energy use. A relatively random application of electrical stimulation intensities may be an effective manner for determining the most effective sub-threshold intensity. In a further example, each of the electrical stimulation signals delivered to the patient (84) (88) (92) (96) are selected from a group of 80%, 60%, 40% and 20% of perception or paresthesia threshold of patient 12.

In some examples, each of the electrical stimulation signals delivered to the patient (84) (88) (92) (96) are delivered in a predetermined order. In some examples, each of the electrical stimulation signals delivered to the patient (84) (88) (92) (96) are delivered in a random order. In some examples, each of the electrical stimulation signals delivered to the patient (84) (88) (92) (96) is delivered for a predetermined period of time, which may be the same or different for each of the electrical stimulation signals delivered to the patient (84) (88) (92) (96). In some examples, each of the electrical stimulation signals delivered to the patient (84) (88) (92) (96) may be delivered for a random period of time.

In some examples, each of the electrical stimulation signals delivered to the patient (84) (88) (92) (96) are within an intensity range of 10% to 80% of the patient's paresthesia or perception threshold. In some examples, each of the electrical stimulation signals delivered to the patient (84) (88) (92) (96) are within an intensity range of 20% to 80% of the patient's paresthesia or perception threshold. In some examples, each of the electrical stimulation signals delivered to the patient (84) (88) (92) (96) are within an intensity range of 20% to 60% of the patient's paresthesia or perception threshold. In some examples, each of the electrical stimulation signals delivered to the patient (84) (88) (92) (96) are within an intensity range of 40% to 60% of the patient's paresthesia or perception threshold. In some examples, each of the electrical stimulation signals delivered to the patient (84) (88) (92) (96) are within an intensity range of 20% to 40% of the patient's paresthesia or perception threshold. In some examples, the lower intensity electrical stimulation signal is approximately 20% of a patient's paresthesia or perception threshold.

Processor 30 may control stimulation generator 34 as described above automatically (e.g., based on a program stored in memory 32) or through a command from a clinician or patient 12 via input device 19. This process may be used to titrate to electrical stimulation signal that is sub-threshold and provides therapeutic relief with lower power consumption. In some examples, this process may include utilizing feedback from patient 12 as discussed with respect to FIG. 8B.

While patient 12 may feel effective pain relief at a sub-threshold electrical stimulation signal that is 99% of the intensity of the paresthesia or perception level, if effective pain relief can be delivered at lower intensities, rechargeable power source 38 would not need to be charged as often. Some patients may be more satisfied by having a lower intensity electrical stimulation signal and not having to charge the rechargeable power source 38 as often, especially if the lower intensity electrical stimulation signal is significantly lower than the paresthesia or perception level. Additionally, some patients may not like feeling paresthesia.

Figure 8B:
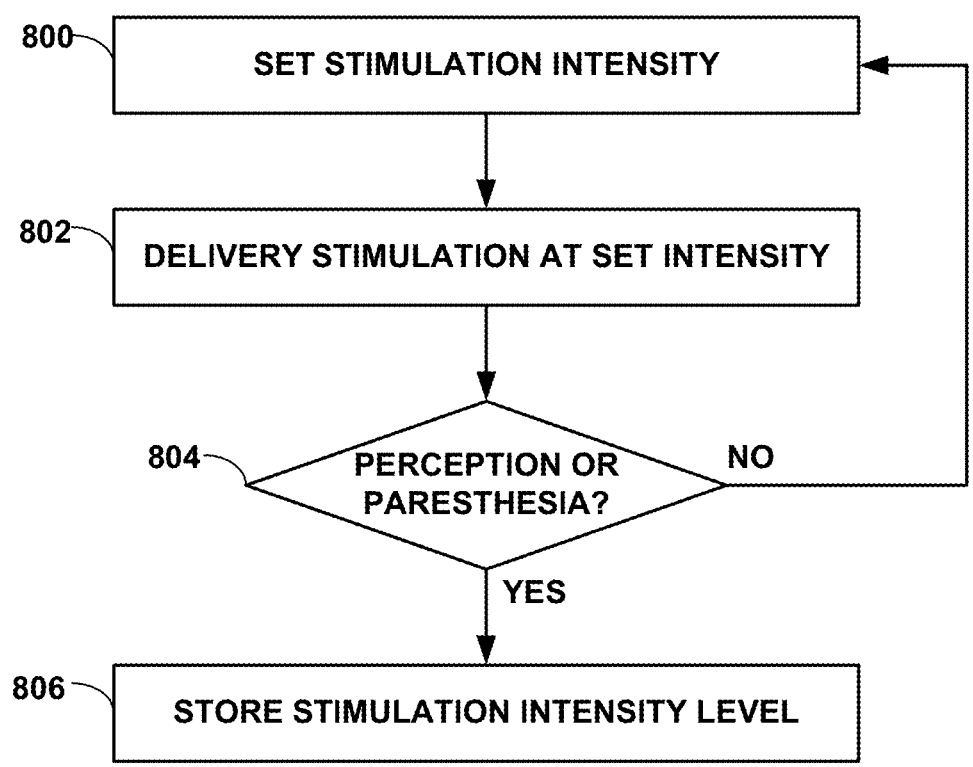

FIG. 8B is a flow diagram of an example technique by which processor 30 of IMD 14 may determine at least one of the perception or paresthesia threshold intensity level for patient 12. In some examples, processor 30 is configured to determine the perception threshold intensity level, while in other examples, processor 30 is configured to determine the paresthesia threshold intensity level or both the perception and paresthesia threshold intensity level.

The perception or paresthesia threshold intensity level can be patient-specific, as well as specific to a target tissue site within patient 12. Thus, a perception or paresthesia threshold intensity level may be determined for each target tissue site to which IMD 14 delivers stimulation therapy. In some examples, processor 30 of input device 19 may implement the technique illustrated in FIG. 8B automatically, e.g., without user intervention or control after initiating the technique. In other examples, processor 30 may implement the technique illustrated in FIG. 8B under control of a user, such as a clinician, who controls processor 30 via input device 19. While FIG. 8B is described with respect to processor 30 of IMD 14, in other examples, processor 50 of input device 19 may perform any part of the technique described with respect to FIG. 8B, alone or in combination with processor 30 of IMD 14.

In accordance with the technique shown in FIG. 8B, processor 30 sets stimulation parameter values such that the stimulation parameter values define a relatively low stimulation intensity, e.g., an intensity below an expected perception or paresthesia threshold intensity (800). Alternatively, the intensity could be set at a higher stimulation intensity. The initial stimulation parameter values may be selected by a clinician in some examples. In some examples in which processor 30 controls stimulation generator 34 to generate and deliver stimulation to patient 12 in the form of electrical pulses, the stimulation parameters include at least one of a voltage or current amplitude, a pulse width, a pulse rate or frequency, or a duty cycle. In examples in which processor 30 controls stimulation generator 34 to deliver stimulation to patient 12 in the form of a continuous waveform, the stimulation parameters include at least one of a voltage amplitude, a current amplitude, a frequency, a waveform shape, or a duty cycle.

Processor 30 sets the stimulation parameters to respective values to define a stimulation intensity, and controls stimulation generator 34 to deliver stimulation to patient 12 at the set stimulation intensity (defined by the selected stimulation parameter values) (802). During therapy delivery or after stimulation generator 34 delivers stimulation to patient 12, processor 30 determines whether patient 12, a clinician, or patient caretaker has provided input indicating patient 12 has perceived the electrical stimulation or indicating paresthesia resulted from the electrical stimulation (804). Patient 12, the clinician, or patient caretaker can provide the input, e.g., via user interface 54 of input device 19 or directly via IMD 14. For example, a motion sensor 37 can be integrated into or on a housing of IMD 14, and the motion sensor 37 can be configured to generate a signal that is indicative of patient 12 tapping IMD 14 through the skin. The number, rate, or pattern of taps may be associated with the input indicative of stimulation perception or paresthesia, and processor 30 may identify the tapping by patient 12 to determine when patient input is received. When the input is received via user interface 54 of input device 19, processor 50 of input device 19 may transmit a signal indicative of the input to IMD 14 via the respective telemetry modules 56, 36.

When processor 30 has not received an indication of the input indicative of the stimulation perception or paresthesia within a predetermined time period during or immediately after delivery of the stimulation according to the selected stimulation intensity ("NO" branch of block 804), processor 30 again sets the stimulation intensity, e.g., by adjusting at least one stimulation parameter value to increase or otherwise change a stimulation intensity of the stimulation signal (800). For example, processor 30 may increase a voltage amplitude or a current amplitude to increase the stimulation intensity. In some examples, processor 30 changes a value of only one of the stimulation parameters while the remaining parameters are kept approximately constant. The stimulation parameter that is selected may be known to affect stimulation intensity. In other examples, processor 30 may adjust a combination of two or more stimulation parameters to increase stimulation intensity.

After modifying the one or more stimulation parameter values, processor 30 controls stimulation generator 34 to deliver stimulation to patient 12 using the newly defined stimulation parameter values (802). In this way, processor 30 can implement an iterative procedure to determine the perception or paresthesia threshold intensity for patient 12, and, in some examples, for a specific target tissue site within patient 12.

In response to not receiving input indicative of patient perception or paresthesia is received within a predetermined time period during or immediately after delivery of the stimulation according to the selected stimulation intensity ("NO" branch of block 804), processor 30 may again adjust at least one stimulation parameter value to increase a stimulation intensity of the stimulation signal (800). This process may repeat until processor 30 receives input indicative of patient perception or paresthesia within a predetermined time period during or immediately after delivery of the stimulation according to the selected stimulation intensity. In response to receiving the input ("YES" branch of block 804), processor 30 may store the stimulation intensity level as the patient perception threshold intensity level and/or paresthesia threshold intensity level (depending on the whether the response indicates patient perception of the electrical stimulation or resulting paresthesia, respectively) in memory 32 of IMD 14 (FIG. 2) or in another memory (e.g., memory 52 of input device 19) (806).

In addition, processor 30 may define stimulation parameter values for the therapy programs 40 (FIG. 2) for providing the electrical stimulation techniques described herein based on the determined patient perception threshold intensity level and/or paresthesia threshold intensity level, e.g., using the technique described with respect to FIG. 8A. For example, processor may define stimulation parameter values for the therapy programs 40 (FIG. 2) that result in a stimulation intensity level significantly less than to one or both of the patient perception threshold intensity level or paresthesia threshold intensity level.

Figure 8C:
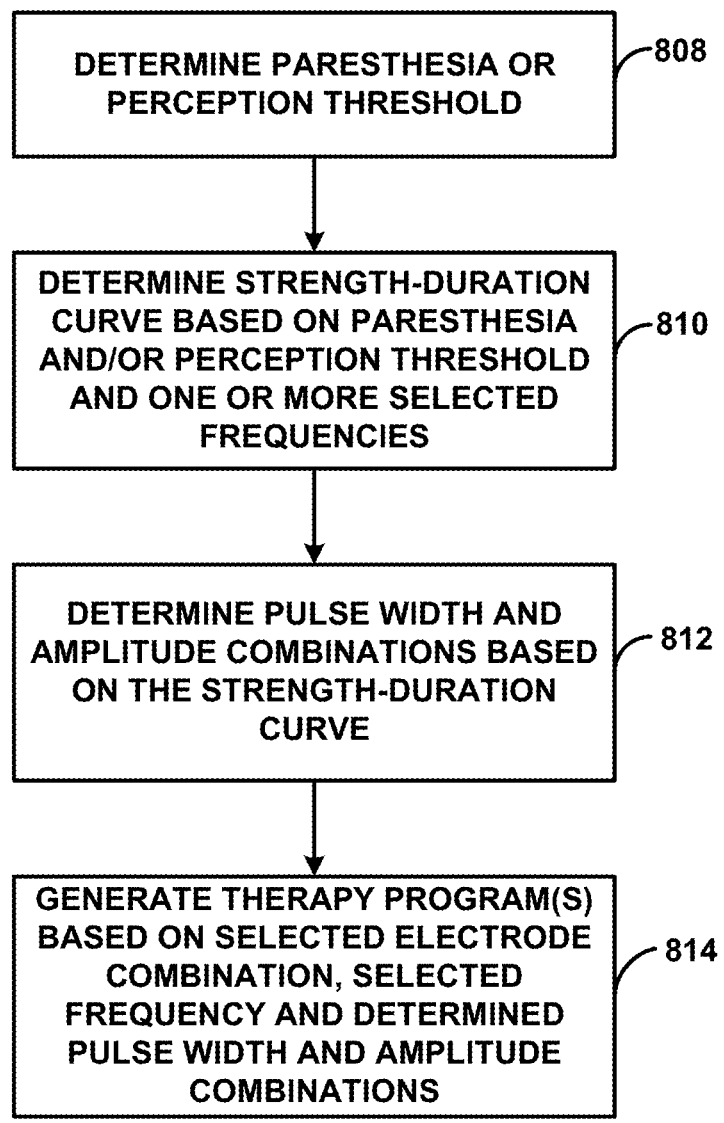

FIG. 8C is a flow diagram of an example method according to techniques of this disclosure. Processor 30 may determine a perception and/or paresthesia threshold as described earlier herein (808). Processor 30 may also determine a strength-duration curve based on the determined one or both of the paresthesia or perception threshold intensity level and one or more selected electrical stimulation signal frequencies (810). A strength-duration curve may describe the relationship between a strength of electrical stimulation and duration, e.g., for a particular physiological response, such as a response below the paresthesia or perception threshold of patient 12. The strength of electrical stimulation may be a function of, for example, any one or more of the voltage or current amplitude value of the stimulation signal, frequency of stimulation signals, signal duration (e.g., pulse width in the case of stimulation pulses), duty cycle, and the like.

An example of a strength duration curve is an amplitude-pulse width curve. The amplitude-pulse width curve may reflect, for a selected stimulation frequency, different combinations of amplitude and pulse width values that contribute to a stimulation field in a substantially similar manner. For example, the amplitude-pulse width curve may indicate that a first electrical stimulation signal with a first amplitude and a first pulse width, and a second electrical stimulation signal having a higher amplitude pulse with a shorter pulse width (i.e., shorter than the first pulse width) may both provide electrical stimulation therapy below the paresthesia or perception threshold of patient 12. Each position on the amplitude-pulse width curve, or each position within a particular range of positions along the amplitude-pulse width curve, may result in a substantially similar stimulation energy when the other therapy parameter values, such as a frequency, remain substantially constant (e.g., the other therapy parameter values may remain within a particular range of therapy parameter values, such as within a 10% window or less from the values defined by the therapy program). Thus, for a given stimulation frequency, the amplitude-pulse width curve may define, e.g., via the amplitude-pulse width combinations associated with the area under the curve and/or along the curve, the amplitude and pulse width combinations that provide electrical stimulation therapy having an intensity level below the paresthesia or perception threshold intensity level of patient 12.

For a given frequency (e.g., in a range of about 1 Hz to about 1000 Hz), based on the strength-duration curve, processor 30 may determine the pulse width and amplitude combination that provides efficacious electrical stimulation therapy to patient 12 and also has a stimulation intensity significantly below the paresthesia or perception threshold of patient 12 (812). Processor 30 may, automatically or in response to user input provided via input device 19, control stimulation generator 34 to generate and deliver electrical stimulation therapy to patient 12 with the frequency associated with the strength-duration curve, a selected combination of electrodes 24, 26, and a plurality of pulse width and amplitude combinations along the strength-duration curve or below the amplitude-pulse width curve. Processor 30 may determine whether any of the selected pulse width and amplitude combinations provides efficacious electrical stimulation therapy for patient 12, e.g., based on patient 12 input or input from another entity received via input device 19, based on input from a sensing module of IMD 14 or a separate sensing module, or any combination thereof. Processor 30 may generate one or more therapy programs based on the one or more pulse width and amplitude combinations that provide efficacious electrical stimulation therapy to patient 12, together with the selected frequency and electrode combination (814).

In some examples in which stimulation generator 34 generates and delivers the sub-threshold electrical stimulation therapy via a plurality of sub-signals delivered via respective electrode combinations, processor 30 may determine a strength-duration curve for each electrode combination. Thus, for each electrode combination, the respective strength-duration curve may indicate a plurality of combinations of electrical stimulation parameters (e.g., amplitude and pulse width for a given frequency) that provide a charge per pulse below the paresthesia or perception threshold of patient 12. Based on the strength-duration curves, processor 30, alone or based on input from a clinician, may determine, for each of the electrode combinations, one or more therapy programs that provide a similar sub-threshold intensity. Each therapy program may define a sub-signal. Processor 30, alone or based on input from a clinician, may then determine a frequency to interleave the two or more sub-signals.

In some examples, to determine the therapy programs, processor 30 may determine one or more test therapy programs that define relatively wide pulse widths and relatively low frequencies of the sub-signals, control stimulation generator 34 to generate and deliver electrical stimulation to patient 12 according to the test therapy programs, and, if the delivered electrical stimulation therapy is not sufficiently efficacious, processor 30 may modify one or more of the test therapy programs until the electrical stimulation provides efficacious stimulation therapy for patient 12. The efficacy of the electrical stimulation therapy can be based on input from patient 12, from one or more sensed physiological parameters, or any combination thereof. Processor 30 may modify one or more of the test therapy programs by, for example, incrementally changing the pulse width (e.g., by a predetermined increment) and/or incrementally changing the frequency (e.g., by a predetermined increment) and/or incrementally changing the amplitude (e.g., by a predetermined increment).

Processor 30 may store the one or more therapy programs 40 in memory 32 of IMD 14 or a memory of another device for later delivery of electrical stimulation therapy to patient 12 (814). Processor 30 may control stimulation generator 34 to generate and deliver electrical stimulation therapy to patient 12 in accordance with the one or more therapy programs 40.

In some cases, therapeutic efficacy of electrical stimulation therapy delivered by IMD 14 may change as the patient posture state (e.g., a particular patient posture or a combination of posture and activity) changes. In some examples, IMD 14 may deliver an electrical stimulation signal that is below patient 12's paresthesia threshold or perception threshold in one posture and when patient 12 moves to another posture that same intensity electrical stimulation signal may be sufficiently intense that the patient perceives the electrical stimulation signal or has paresthesia. Efficacy may refer to a combination of complete or partial alleviation of symptoms alone, or in combination with no side effects or an acceptable or tolerable degree of undesirable side effects. In some examples, processor 30 of IMD 14 may be configured to adjust one or more therapy parameter values based on different postures and/or activities engaged by patient 12 to maintain effective therapy, e.g., by selecting select different therapy programs based on a posture state of patient 12. In these examples, processor 30 may determine the paresthesia or perception threshold of patient 12 for each of a plurality of different posture states and determine one or more therapy programs 40 for each of the posture states using the technique shown in FIG. 8D based on the respective paresthesia or perception threshold.

Figure 8D:
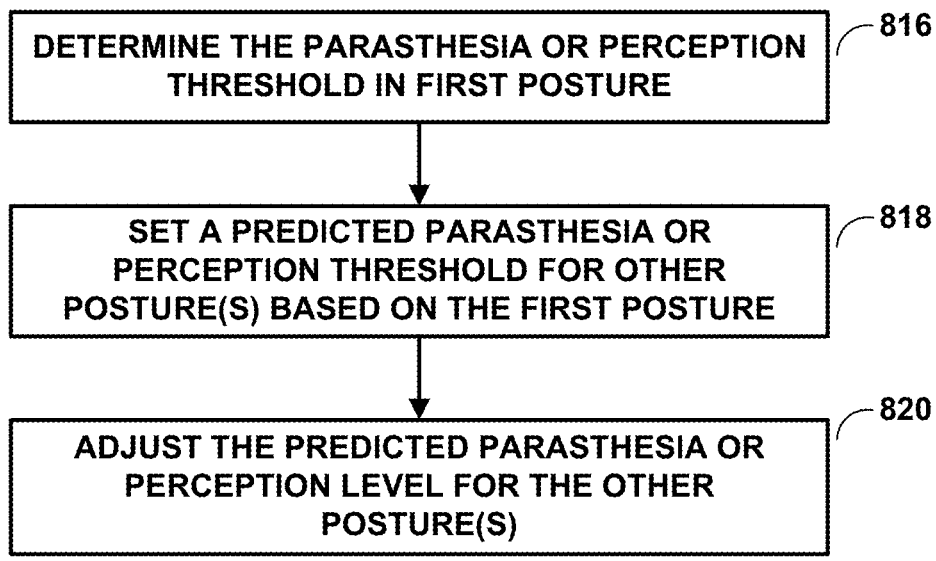

FIG. 8D is a flow diagram depicting a method of determining different intensity levels of therapies according to techniques of this disclosure. Processor 30 may determine the paresthesia or perception threshold of patient 12 in a first posture, for example, standing (816) in a manner discussed above and store it in memory 32. From the paresthesia or perception threshold in the first position, processor 30 may derive predicted paresthesia or perception thresholds for other postures (818). For example, processor 30 may calculate the predicted paresthesia or predicted perception thresholds or processor 30 may use a look-up table that may be stored in memory 32. In one example, processor 30 may set the predicted paresthesia or predicted perception thresholds as follows: mobile—the same as standing; sitting—the same as standing; reclining—30% less than standing; lying on back—30% less than standing; lying on front—30% less than standing; lying on left side—30% less than standing; lying on right side—30% less than standing. Processor 30 may store the predicted paresthesia or perception thresholds in memory 32.

Processor 30 may utilize the predicted paresthesia or perception thresholds to determine the stimulation signal intensity for one or more of the other postures. Processor 30 may calculate the stimulation signal intensity for the one or more other postures or may look it up on a look-up table in memory 32. Processor 30 may store the stimulation signal intensities for the one or more other positions in memory 32 or may store therapy programs based on the one or more other positions in memory 32. The stimulation signal intensity may be varied for the one or more other postures as described above with regard to FIG. 8A.

Over time, processor 30 may adjust the predicted paresthesia or predicted perception thresholds for the other postures (820). For example, processor 30 may automatically deviate the intensity of the therapy when patient 12 is in the other postures and wait for feedback from the patient 12 or a physician or clinician on input device 19. Alternatively, processor 30 may utilize the predicted paresthesia or predicted perception thresholds as if they were fixed until it receives feedback from input device 19 indicating that one or more of the predicted paresthesia or predicted perception thresholds needs to be adjusted. For example, patient 12 may indicate through input device 19 that they are feeling paresthesia. Processor 30 may then control stimulation generator 34 to lower the intensity of the stimulation signal, lower the predicted paresthesia or predicted perception threshold accordingly and store the lowered predicted paresthesia or lowered predicted perception threshold in memory 32. Processor 30 may lower the predicted paresthesia or predicted perception threshold by calculating a new predicted threshold or by looking it up on a lookup table stored in memory 32, for example.

Figure 8E:
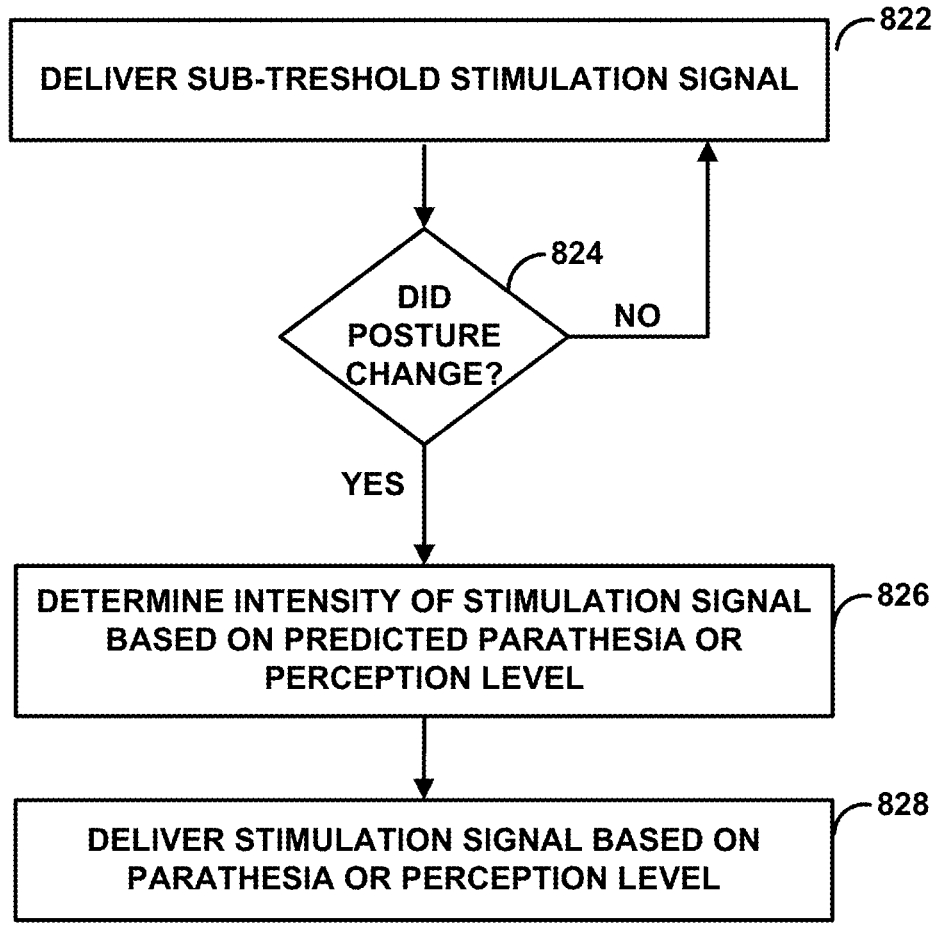

FIG. 8E is a flow diagram depicting a method of automatically adjusting the intensity of an electrical stimulation signal based on a change in posture. IMD 14 may deliver a sub-threshold electrical stimulation signal to patient 12 (822). For example, the sub-threshold electrical stimulation signal may have an intensity that is a percentage of patient 12's paresthesia threshold or perception threshold. Processor 30 of IMD 14 may determine whether patient 12 has changed postures (824), for example by monitoring a signal from motion sensor 37, such as an accelerometer. Details on how to determine a change in posture based on an accelerometer signal can be found in commonly-assigned U.S. patent application Ser. No. 15/607,945, titled, "ACCELEROMETER SIGNAL CHANGE AS A MEASURE OF PATIENT FUNCTIONAL STATUS," filed May 25, 2017, now published as US Patent Application Publication No. US 2018/0035924 A1 and claiming the benefit of Provisional Application No. 62/370,138, filed on Aug. 2, 2016, the entire content of which is incorporated by reference herein. If processor 30 of IMD 14 does not determine that there has been a change posture of patient 12 (the "NO" path from decision diamond 824) IMD 14 may continue to deliver the sub-threshold electrical stimulation signal. If processor 30 of IMD 14 does determine that there has been a change in posture of patient 12 (the "YES" path from decision diamond 824) IMD 14 may determine a different intensity of the electrical stimulation signal based on the predicted paresthesia level or predicted perception level (826). For example, if patient 12 is standing and IMD 14 is delivering a sub-threshold electrical stimulation signal to patient 12 of X intensity and then patient 12 lies down, IMB 14 may detect the change in posture and reduce the intensity of the electrical stimulation signal by 30%. IMB 14 may deliver the different intensity electrical stimulation signal to patient 12 (828). IMD 14 may ramp the intensity of the electrical stimulation signal up or down to arrive at the different intensity electrical stimulation signal. Alternatively, IMD 14 may switch from the sub-threshold intensity to the different intensity without a ramp up or down.

Figure 9:
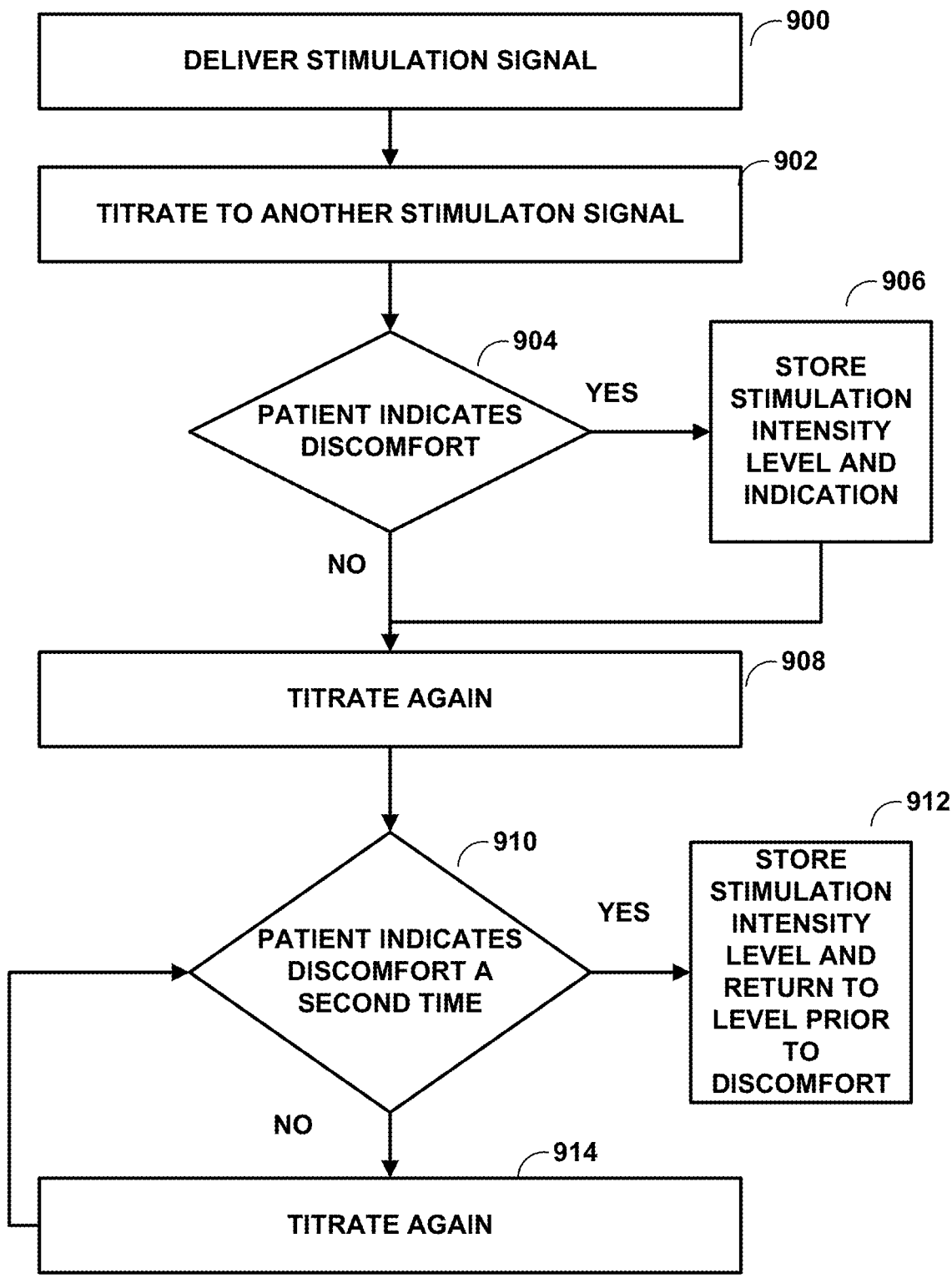
FIG. 9 is a flow diagram of the use of patient feedback according to techniques of this disclosure.

FIG. 9 is a flow diagram describing the use of patient feedback according to techniques of the present disclosure. When titrating between different stimulation signal intensities as described above with respect to FIG. 8A, it may be desirable to enable patient 12 to provide input on input device 19, for example, on their level of discomfort or dissatisfaction. Processor 30 of IMD 14 may take the input from input device 19 and take action based on that input. For example, processor 30 may cause stimulation generator 34 to deliver a stimulation signal of a particular intensity to patient 12 through electrodes 24 and/or 26 (900). Processor 30 may then titrate that stimulation to another intensity level (902). Processor 30 may then await input from patient 12, for example, such as whether or not patient 12 experiencing discomfort or is the patient dissatisfied with the treatment (904). If patient 12 indicates they are in discomfort or dissatisfied on input device 19, for example, processor 30 may store the current intensity level and the indication that patient 12 was in discomfort or dissatisfied at that level in memory 32 (906). In some examples, processor 30 may then change the intensity of the stimulation signal back to the original intensity of block 900. In other examples, processor 30 may continue to titrate the intensity of the stimulation signal generated by stimulation generator 34 (908). Processor 30 may then wait again for input from patient 12 on input device 19, for example (910). If patient 12 provides a second indication on input device 19, for example, that they are in discomfort or dissatisfied with the treatment, processor 30 may store that indication and the current stimulation intensity in memory 30 and return to an intensity at which the patient did not indicate they were in discomfort or dissatisfied (912). If patient 12 does not provide an indication that they are in discomfort or dissatisfied, processor 30 may cause stimulation generator 34 to titrate again (914). This may continue until patient 12 has indicated they are in discomfort or dissatisfied twice. In one example, this continues until patient 12 indicates they are in discomfort or dissatisfied at two consecutive intensity levels.

Processor 30 may perform the functions described with respect to FIG. 9 automatically (e.g., based on a program stored in memory 32) without a clinician involved or through input from a clinician using input device 19, for example.

Figure 10:
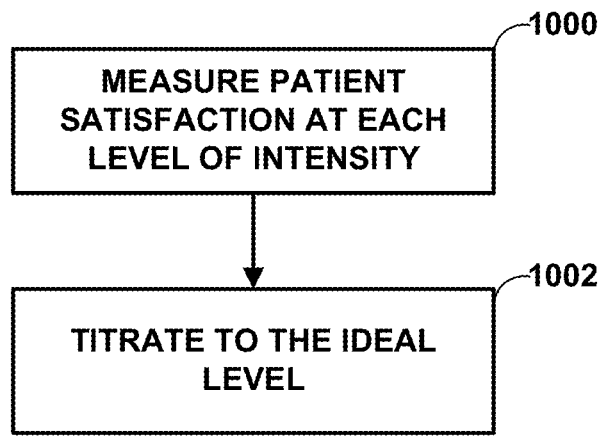
FIG. 10 is a flow diagram of another example of the use of patient feedback according to techniques of this disclosure.

FIG. 10 is a flow diagram describing another use of patient feedback according to techniques of the present disclosure. These techniques can be used with other techniques described herein, such as those described with respect to FIG. 8A. In some examples, at each intensity level and/or for each posture, patient 12 may provide feedback to IMD 14 through input device 19 about their level of satisfaction or comfort (1000). For example, patient 12 may indicate one or more of they are feeling the treatment, they are feeling the treatment all the time or some of the time, they are uncomfortable, and/or they are feeling similar pain relief to a previous intensity level. Processor 30 may store this information, the intensity level of the stimulation signal and/or the posture in memory 32 and control stimulation generator 34 to titrate the stimulation signal to the ideal intensity level for patient 12, in a given posture, for example (1002). Processor 30 may utilize the patient input to calculate the ideal intensity or may utilize a look-up table to arrive at the ideal intensity.

Processor 30 may perform the functions described with respect to FIG. 10 automatically (e.g., based on a program stored in memory 32) or through input from a clinician using input device 19, for example.

Figure 11:
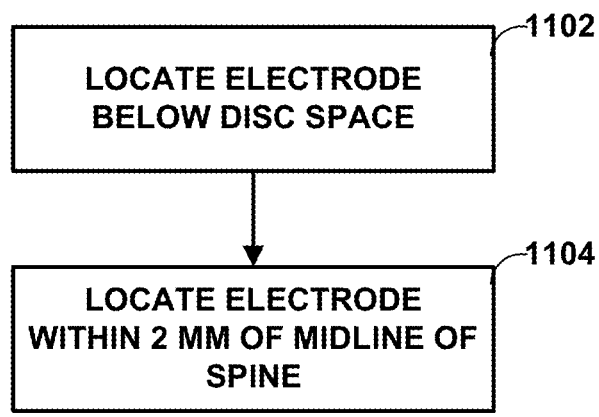
FIG. 11 is a flow diagram of an example method of locating electrodes according to techniques of this disclosure.

FIG. 11 is a flow diagram describing where a physician or clinician should place electrodes 24 and/or 26 or which of electrodes 24A-24D and/or 26A-26D should be active for treatment for better efficacy. As demonstrated in a study discussed below patients felt better pain relief, had higher perception thresholds and responded better to treatment at intensities significantly below perception level when electrodes are placed below the T9-10 spinal disc space in a lateral view and within 2 mm of the midline of the spine in an anterior/posterior or posterior/anterior view. A physician or clinician may locate one or both of electrodes 24 and 26 or program IMD 14 to deliver electrical stimulation through one or more of electrodes 24A-D and 26A-D below a spinal disc space, such as the T9-10 disc space (1102). The physician may also locate one or both of electrodes 24 and 26 or program IMD 14 to deliver electrical stimulation through one or more of electrodes 24A-D and 26A-D within 2 mm of the midline of the spine (1104). The physician or clinician may perform the location of electrodes 24 and 26 through an implantation procedure, a relocation procedure or simply through external placement. IMD 14 may be more effective by delivering a sub-threshold stimulation signal below the T9-10 spinal disc space in a lateral view and by delivering a sub-threshold stimulation signal within 2 mm of the midline of the spine in an anterior/posterior or posterior/anterior view.

Figure 12:
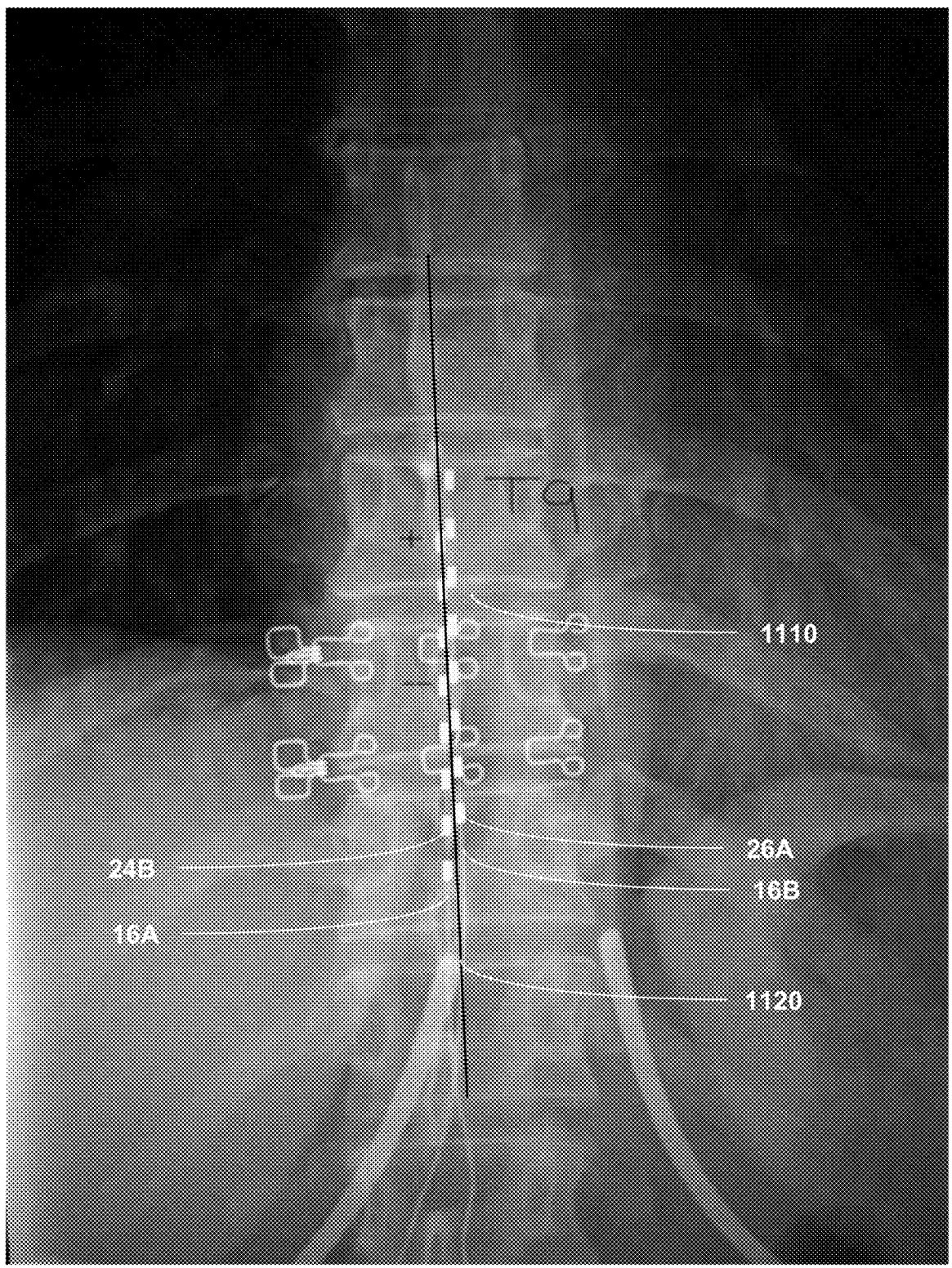
FIG. 12 is a diagram illustrating the location of electrodes in a patient according to techniques of this disclosure.

FIG. 12 is a diagram illustrating the location of electrodes in a patient according to techniques of this disclosure. Leads 16A and 16B are disposed generally laterally to midline of the spine 1120 of patient 12. Electrodes of leads 16A and 16B (e.g., electrode 24B and electrode 26A) may be located within 2 mm of the midline of spine 1120 of patient 12 in a lateral view. In the example of FIG. 12 some of the electrodes (such as electrode 24B and electrode 26A) are located below the T9-T10 disc space 1110 in an anterior/posterior or posterior/anterior view. In this example, a physician or clinician may program IMD 14 to deliver electrical stimulation to patient 12 through electrodes located below the T9-T10 disc space 1110 (such as electrode 24B and electrode 26A). Alternatively, a physician may relocate the leads 16A and 16B so more or all of the electrodes 24 and 26 are located below the T9-T10 disc space 1110.

A recently commissioned study attempted to characterize a minimum amplitude level needed to maintain therapy satisfaction and pain relief when stimulating with a pulse width of 90 µs and a frequency of 1000 Hz.

This study was a prospective, multi-center, single-blind, study characterizing the minimum amplitude maintaining SCS therapy that is satisfying and provides pain relief. Qualified patients had back and leg pain, a RestoreSensor™ system, by Medtronic plc, with electrical stimulation parameters of 1000 Hz and 90 µs, and were very or somewhat satisfied with the therapy, and an average overall visual analogue pain score (VAS) of ≤4 (0-10 scale) from a daily diary each of the patients kept.

The patients received four blinded amplitudes (titrated from 80%, 60%, 40%, and 20% of perception threshold), approximately two weeks each, with electrical stimulation parameters of 90 microseconds pulse width, a frequency of 1000 Hz, a bipole, and had AdaptiveStim™ technology by Medtronic plc enabled. Patients' satisfaction and overall VAS pain scores were collected for each period. Thirty qualified patients, from 7 U.S. sites, (76.7% females, mean age 65.1, 76.7% Failed Back Surgery Syndrome/post-surgical back and leg pain) had chronic pain an average 15.0 years (standard deviation, SD 13.5) and an SCS implant for an average 1.9 years (SD 1.3).

The perception thresholds of the patient's in the study ranged from 0.7 volts to 9.7 volts in the sitting position and from 0.35 volts to 9.7 volts in the supine position.

The minimum amplitude which maintained therapy satisfaction was 80% of perception threshold for 2 patients (6.7%), 60% for 1 patient (3.3%), and 20% for 21 patients (70%). In addition, 6 patients (20%) lost satisfaction changing from their baseline amplitude to 80% perception threshold.

The minimum amplitude which maintained overall pain relief was 80% of perception threshold for 3 patients (10.0%), 60% for 1 patient (3.3%), 40% for 2 patients (6.7%), and 20% for 19 patients (63.3%). In addition, 5 patients (16.7%) had >2 increase in overall VAS changing from their baseline amplitude to 80% perception threshold.

These implanted patients defined a population reporting good pain relief and satisfaction using HD SCS therapy at baseline, where baseline was the amplitude for which the device was set when the patient joined the study. The majority of patients maintained therapy satisfaction and pain relief at an amplitude of only 20% of perception threshold. These results support that effective SCS therapy may be maintained at amplitudes significantly below perception threshold in these patients. Interestingly, some patients reported better pain relief and satisfaction at a lower amplitude than they did at a higher amplitude during the titration.

Understanding the spinal target electrode location for spinal cord stimulation (SCS) is also important for discerning the effects on pain relief and power consumption.

During the study, images (fluoroscopy and x-rays) were taken and analyzed to determine the location of the active electrodes. Cathodes were characterized in relation to the midline of the spine (from an anterior/posterior or posterior/anterior view) and T9-10 vertebrae disc space (from a lateral view). Furthermore, the overall VAS pain score was characterized at each amplitude level, as a percentage of perception threshold, based on cathode location relative to the midline of the spine and T9-10 vertebrae disc space. Table 1 below shows the results of this portion of the study, where V represents the perception threshold in volts, SD represents the standard deviation and n represents the number of patients.

TABLE 1

| Category | Distance (mm) from landmark (mean ± SD) | Baseline perception threshold (V) sitting (mean ± SD, n*) | Baseline perception threshold (V) supine (mean ± SD, n*) |
|---|---|---|---|
| Cathode relative to midline | | | |
| >2 mm of midline (n = 9) | 3.6 ± 1.4 | 2.7 ± 1.6, 7 | 3.3 ± 3.2, 8 |
| ≤2 mm of midline (n = 20) | 0.9 ± 0.6 | 5.6 ± 2.1, 17 | 4.2 ± 1.9, 19 |
| Cathode relative to T9-10 disc space | | | |
| Above (n = 8) | 6.0 ± 3.8 | 3.9 ± 1.8, 7 | 2.6 ± 1.5, 7 |
| Below (n = 16) | 3.9 ± 3.9 | 5.5 ± 2.7, 12 | 4.9 ± 2.5, 15 |

*not all patients reached perception threshold

Figure 13A:
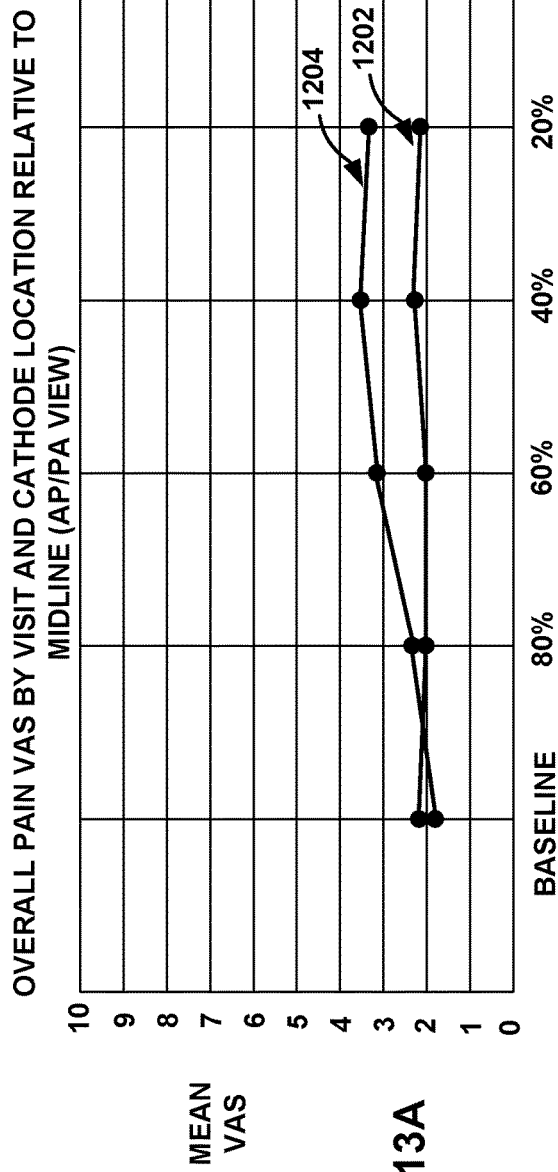
FIGS. 13A and 13B are graphs depicting the average VAS pain scores for patients in a recent study.

FIG. 13A is a graph depicting the average VAS pain score for patients in the study with cathodes ≤2 mm of midline (1202) compared to those with cathodes >2 mm of midline (1204) at each amplitude titration point. As can be seen, patients with cathodes ≤2 mm of midline of the spine had higher amplitude perception thresholds and maintained lower overall VAS pain scores, as the amplitude was titrated down, compared to those with cathodes >2 mm of midline. As mentioned earlier, baseline was the amplitude the device was set to when the patient entered the study, it was not the perception threshold. This may be because the spinal cord is able to tolerate a higher dose of energy closer to the midline. Further away from the midline may come closer to nerve roots causing the patient to be more sensitive to the stimulation and thereby only be able to tolerate a smaller, less effective, dose.

The more lateral from midline, the spine may have more C fibers (unmyelinated) with A delta and A beta fibers being closer to midline. It may be more desirable to target the myelinated fibers closer to midline with the electronic stimulation.

Figure 13B:
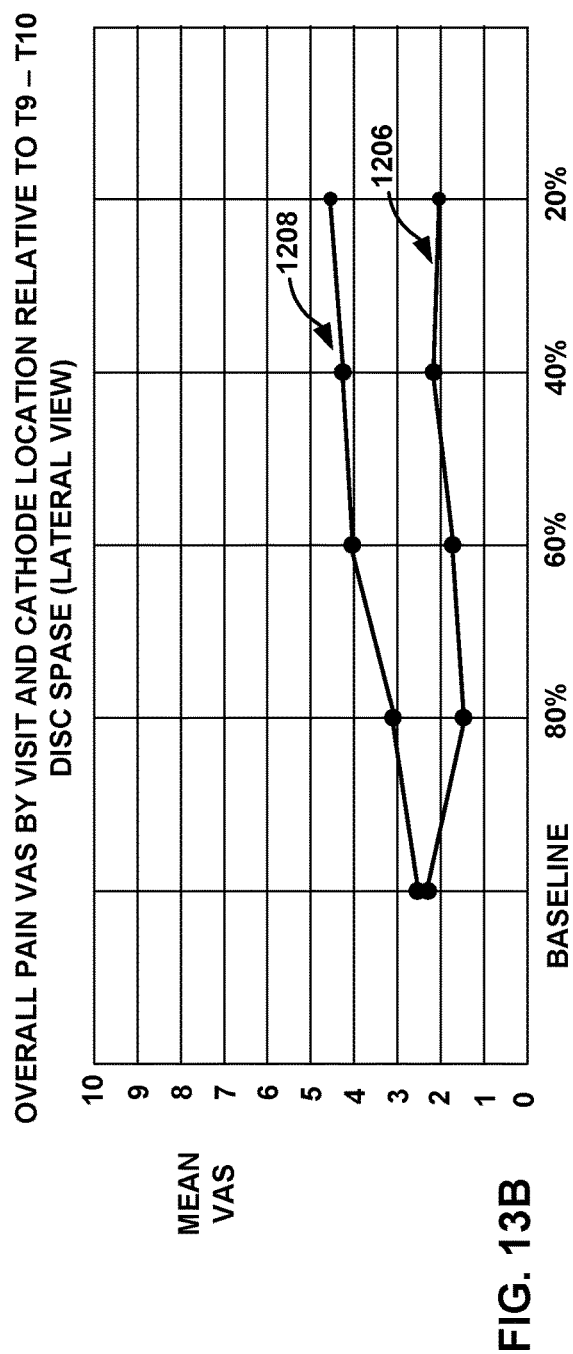

FIG. 13B is a graph depicting the average VAS pain score for patients in the study with cathodes below the T9-10 spinal disc space (1206) compared with those with cathodes above the T-9-10 spinal disc space (2108). As can be seen, patients with cathodes lower than the T9-10 spinal disc space had higher amplitude perception thresholds and maintained lower overall VAS pain scores, as the amplitude was titrated down, compared to those with cathodes above the T9-10 spinal disc space. There may be a physiological reason the electronically stimulating below the spinal disc space is more effective than stimulating above it. These results demonstrate that the location of the electronic stimulation cathode impacts the efficacy of the treatment.

The results of the study show that amplitudes significantly lower than perception threshold (and by implication, paresthesia threshold) were effective at relieving pain in most patients. Additionally, the results showed that location of the cathodes could improve efficacy. Furthermore, although not present in the above chart, the study showed that there is a correlation between the perception threshold when the patient is in different postures. For example, when the patient is supine, the perception threshold is on the order of approximately 30% less than when the patient is sitting. The techniques of the present disclosure may lead to lower power consumption, while still providing effective pain relief to patients, extending time between battery charges and/or extending battery life.

While this study was performed utilizing an electrical stimulation signal having a pulse width of 90 µs, a frequency of 1000 Hz and varying voltage amplitudes, the techniques of this disclosure may be utilized with current amplitudes rather than voltage amplitudes and/or other pulse widths and frequencies. In some examples utilizing current rather than voltage, a paresthesia or perception level may be very high for higher frequencies and low pulse widths, for instance up to 25.5 mA. In other examples, a paresthesia or perception level may be very low for low frequencies and large pulse widths, for instance 0.1 mA.

In some examples, frequencies between 10 Hz and 500 kHz may be used in accordance with the techniques of this disclosure. In some examples, pulse widths in the range of 25 µs to 2.5 ms may be used in accordance with the techniques of this disclosure.

The techniques described above that are described as being performed by processor 30 of IMD 14 or processor 50 of input device 19 may be performed by either one of the processors or a combination of both. In other examples, one or more other processors may perform any part of the techniques described herein alone or in addition to processor 30 or processor 50. Thus, reference to "a processor" may refer to "one or more processors." Likewise, "one or more processors" may refer to a single processor or multiple processors in different examples.

The techniques described in this disclosure, including those attributed to IMD 14, input device 19, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Each of the techniques described herein may be used separately, together or in any combination. Various aspects of the techniques of this disclosure may enable one or more of the devices described above to perform the examples listed below.

Example 1. A method comprising: generating, by a medical device, a lower intensity electrical stimulation signal comprising a plurality of pulses, wherein the lower intensity electrical stimulation signal has a stimulation intensity that is significantly lower than a paresthesia threshold or perception threshold of a patient; and delivering, by the medical device, the lower intensity electrical stimulation signal to the patient.

Example 2. The method of example 1, further comprising: generating a first intensity electrical stimulation signal comprising a plurality of pulses; delivering, by the medical device, the first intensity electrical stimulation signal to the patient; and titrating from first intensity electrical stimulation signal to the lower intensity electrical stimulation signal.

Example 3. The method of example 2, further comprising: generating a second intensity electrical stimulation signal comprising a plurality of pulses; and delivering, by the medical device, the second intensity electrical stimulation signal to the patient; wherein titrating from the first intensity electrical stimulation signal to the lower intensity electrical stimulation signal comprises titrating from the first intensity electrical stimulation signal to the second intensity electrical stimulation signal and titrating from the second intensity electrical stimulation signal to the lower intensity electrical stimulation signal.

Example 4. The method of example 3, further comprising: generating a third intensity electrical stimulation signal comprising a plurality of pulses; and delivering, by the medical device, the third intensity electrical stimulation signal to the patient; wherein titrating from the first intensity electrical stimulation signal to the lower intensity electrical stimulation signal comprises titrating from the first intensity electrical stimulation signal to the second intensity electrical stimulation signal, titrating from the second intensity electrical stimulation signal to the third intensity electrical stimulation signal, and titrating from the third intensity electrical stimulation signal to the lower intensity electrical stimulation signal.

Example 5. The method of example 4, wherein the first intensity electrical stimulation signal, the second intensity electrical stimulation signal, and the third intensity electrical stimulation signal are different from each other.

Example 6. The method of any combination of examples 1-5, wherein the lower intensity electrical signal is less than or equal to 60% of at least one of the paresthesia threshold or perception threshold of the patient.

Example 7. The method of any combination of examples 1-6, wherein the lower intensity electrical signal is less than or equal to 40% of at least one of the paresthesia threshold or perception threshold of the patient.

Example 8. The method of any combination of examples 1-7, wherein the lower intensity electrical signal is less than or equal to 20% of at least one of the paresthesia threshold or perception threshold of the patient.

Example 9. The method of any combination of examples 1-8, wherein the lower intensity electrical signal is within the range of about 10% to 80% of at least one of the paresthesia threshold or perception threshold of the patient.

Example 10. The method of any combination of examples 1-9, wherein the lower intensity electrical signal is within the range of about 20% to 80% of at least one of the paresthesia threshold or perception threshold of the patient.

Example 11. The method of any combination of examples 1-10, wherein the lower intensity electrical signal is within the range of about 20% to 60% of at least one of the paresthesia threshold or perception threshold of the patient.

Example 12. The method of any combination of examples 1-7 and 9-11, wherein the lower intensity electrical signal is within the range of about 40% to 60% of at least one of the paresthesia threshold or perception threshold of the patient.

Example 13. The method of any combination of examples 1-12, wherein the lower intensity electrical signal is within the range of about 20% to 40% of at least one of the paresthesia threshold or perception threshold of the patient.

Example 14. The method of any combination of examples 1-11 and 13, wherein the lower intensity electrical signal is within the range of about 20% to 40% of at least one of the paresthesia threshold or perception threshold of the patient.

Example 15. The method of any combination of examples 2-14, wherein titrating is automatic.

Example 16. The method of any combination of examples 2-15, further comprising: receiving an input from the patient to reverse titrating to an earlier intensity electrical stimulation signal; and reverse titrating to the earlier intensity electrical stimulation signal based on the input from the patient.

Example 17. The method of example 16, further comprising: reverse titrating only if the patient provides input to reverse titrating during delivery of two consecutive and different of the first intensity electrical stimulation signal, the second intensity electrical stimulation signal, the third intensity electrical stimulation signal and the lower intensity electrical stimulation signal.

Example 18. The method of any combination of examples 2-17, wherein at least one of an order of titration between electrical stimulation signals, and a time between titrations is random.

Example 19. The method of any combination of examples 2-17, wherein an order of titration between electrical stimulation signals, and a time between titrations is predetermined.

Example 20. The method of any combination of examples 2-19, further comprising determining an ideal intensity of an electrical stimulation signal based on feedback from the patient.

Example 21. The method of example 20, wherein the feedback from the patient is based on a level of satisfaction of the patient for each intensity electrical stimulation signal.

Example 22. The method of example 21, wherein the level of satisfaction of the patient is measured through at least one of whether the patient feels stimulation for each intensity electrical stimulation signal, whether the patient feels stimulation some of the time or all of the time for each intensity electrical stimulation signal, whether the patient is uncomfortable for each intensity electrical stimulation signal, and whether the patient is experiencing similar pain relief for each intensity electrical stimulation signal.

Example 23. The method of any combination of examples 20-22, wherein determining the ideal intensity comprises determining the ideal intensity automatically, and wherein titrating comprises titrating to the ideal intensity automatically.

Example 24. The method of any combination of examples 1-23, wherein the lower intensity electrical stimulation signal has a frequency of about 1000 Hertz.

Example 25. The method of any combination of examples 1-24, wherein the lower intensity electrical stimulation signal has a pulse width of about 90 microseconds.

Example 26. The method of any combination of examples 1-25, wherein generating the lower intensity electrical stimulation signal comprises generating a plurality of sub-signals and interleaving the plurality of sub-signals.

Example 27. The method of example 26, wherein the plurality of sub-signals comprises a first sub-signal and a second sub-signal.

Example 28. The method of any combination of examples 1-27, further comprising: determining, based on a strength-duration curve for the paresthesia threshold or perception threshold, a set of one or more electrical stimulation parameter values for generating the lower intensity electrical stimulation signal.

Example 29. A method of any combination of examples 1-28, wherein: delivering the lower intensity electrical stimulation signal comprises delivering the lower intensity electrical stimulation via at least one electrode near a spine of the patient, the at least one electrode being coupled to the medical device, below a T9-10 spinal disc space in a lateral view.

Example 30. A method of any combination of examples 1-29, wherein: delivering the lower intensity electrical stimulation signal comprises delivering the lower intensity electrical stimulation signal via at least one electrode near a spine of the patient, the at least one electrode being coupled to the medical device, within 2 millimeters of a midline of the spine of the patient in an anterior/posterior or posterior/anterior view.

Example 31. A system comprising: a stimulation generator configured to generate and deliver electrical stimulation therapy to a patient via at least one electrode; and a processor configured to control the stimulation generator to: generate a lower intensity electrical stimulation signal comprising a plurality of pulses, wherein the lower intensity electrical stimulation signal has a stimulation intensity significantly lower than a paresthesia threshold or perception threshold of the patient; and deliver the lower intensity electrical stimulation signal to the patient.

Example 32. The system of example 31, wherein the processor is further configured to control the stimulation generator to: generate a first intensity electrical stimulation signal comprising a plurality of pulses; deliver the first intensity electrical stimulation signal to the patient; and titrate from first intensity electrical stimulation signal to the lower intensity electrical stimulation signal.

Example 33. The system of example 32, wherein the processor is further configured to control the stimulation generator to: generate a second intensity electrical stimulation signal comprising a plurality of pulses; and deliver the second intensity electrical stimulation signal to the patient; wherein titration from the first intensity electrical stimulation signal to the lower intensity electrical stimulation signal comprises titrating from the first intensity electrical stimulation signal to the second intensity electrical stimulation signal and titrating from the second intensity electrical stimulation signal to the lower intensity electrical stimulation signal.

Example 34. The system of example 33, wherein the processor is further configured to control the stimulation generator to: generate a third intensity electrical stimulation signal comprising a plurality of pulses; and deliver the third intensity electrical stimulation signal to the patient; wherein titration from the first intensity electrical stimulation signal to the lower intensity electrical stimulation signal comprises titrating from the first intensity electrical stimulation signal to the second intensity electrical stimulation signal, titrating from the second intensity electrical stimulation signal to the third intensity electrical stimulation signal, and titrating from the third intensity signal to the lower intensity electrical stimulation signal.

Example 35. The system of example 34, wherein the first intensity electrical stimulation signal, the second intensity electrical stimulation signal and the third intensity electrical stimulation signal are different from each other.

Example 36. The system of any combination of examples 31-35, wherein the lower intensity electrical stimulation signal is less than or equal to 60% of at least one of the paresthesia threshold or perception threshold for a patient.

Example 37. The system of any combination of examples 31-36, wherein the lower intensity electrical stimulation signal is less than or equal to 40% of at least one of the paresthesia threshold or perception threshold for a patient.

Example 38. The system of any combination of examples 31-37, wherein the lower intensity electrical stimulation signal is less than or equal to 20% of at least one of the paresthesia threshold or perception threshold for a patient.

Example 39. The system of any combination of examples 31-38, wherein the lower intensity electrical stimulation signal is in the range of about 10% to 80% of at least one of the paresthesia threshold or perception threshold for a patient.

Example 40. The system of any combination of examples 31-29, wherein the lower intensity electrical stimulation signal is in the range of about 20% to 80% of at least one of the paresthesia threshold or perception threshold for a patient.

Example 41. The system of any combination of examples 31-40, wherein the lower intensity electrical stimulation signal is in the range of about 20% to 60% of at least one of the paresthesia threshold or perception threshold for a patient.

Example 42. The system of any combination of examples 31-37 and 39-41, wherein the lower intensity electrical stimulation signal is in the range of about 40% to 60% of at least one of the paresthesia threshold or perception threshold for a patient.

Example 43. The system of any combination of examples 31-42, wherein the lower intensity electrical stimulation signal is in the range of about 20% to 40% of at least one of the paresthesia threshold or perception threshold for a patient.

Example 44. The system of any combination of examples 32-43, wherein the processor is further configured to control the stimulation generator to titrate automatically.

Example 45. The system of any combination of examples 32-44, wherein the processor is further configured to: receive an input from the patient to reverse the titration to an earlier intensity electrical stimulation signal; and control the stimulation generator to reverse the titration to the earlier intensity electrical stimulation signal based on the input from the patient.

Example 46. The system of example 45, wherein the processor is further configured to control the stimulation generator to reverse the titration only if the patient provides input to reverse the titration during delivery of two consecutive and different of the first intensity electrical stimulation signal, the second intensity electrical stimulation signal, the third intensity electrical stimulation signal and the lower intensity electrical stimulation signal.

Example 47. The system of any combination of examples 32-46, wherein the processor is further configured to control the stimulation generator to randomize at least one of an order of titration between electrical stimulation signals, and a time between titrations.

Example 48. The system of any combination of examples 32-46, wherein the processor is further configured to control the stimulation generator to deliver electrical stimulation signals in a predetermined order and to titrate between electrical stimulation signals at a predetermined time.

Example 49. The system of any combination of examples 32-48, wherein the processor is further configured to determine an ideal intensity based on feedback from the patient.

Example 50. The system of example 49, wherein the feedback from the patient is based on a level of satisfaction of the patient for each intensity electrical stimulation signal.

Example 51. The system of example 50, wherein the level of satisfaction of the patient is based on at least one of whether the patient feels stimulation for each intensity electrical stimulation signal, whether the patient feels stimulation some of the time or all of the time for each intensity electrical stimulation signal, whether the patient is uncomfortable for each intensity electrical stimulation signal, and whether the patient is feeling similar pain relief for each intensity electrical stimulation signal.

Example 52. The system of any combination of examples 49-51, wherein the processor is configured to control the stimulation generator to titrate to the ideal intensity automatically.

Example 53. The system of any combination of examples 31-52, wherein the processor is further configured to determine the paresthesia threshold or perception threshold for the patient in a first posture.

Example 54. The system of example 53, wherein the processor is further configured to automatically set a predicted paresthesia threshold or predicted perception threshold for the patient in a second posture based on the paresthesia threshold or perception threshold for the patient in the first posture.

Example 55. The system of example 54, wherein the processor is further configured to set the predicted paresthesia threshold or predicted perception threshold for the patient in the second posture at about 30% different than the paresthesia threshold or perception threshold for the patient in the first posture.

Example 56. The system of any combination of examples 54 and 55, wherein the processor is further configured to adjust the predicted paresthesia threshold or predicted perception threshold for the patient in the second posture based on feedback from the patient.

Example 57. The system of any combination of examples 54 and 55, wherein the processor is further configured to adjust the predicted paresthesia threshold or predicted perception threshold for the patient in the second posture automatically.

Example 58. The system of any combination of examples 31-57, wherein the lower intensity electrical stimulation signal has a frequency of about 1000 Hertz.

Example 59. The method of any combination of examples 31-58, wherein the lower intensity electrical stimulation signal has a pulse width of about 90 microseconds.

Example 60. The system of any combination of examples 31-59, wherein the processor is configured to control the stimulation generator to generate the lower intensity electrical stimulation signal by: generating a plurality of sub-signals; and interleaving the plurality of sub-signals.

Example 61. The system of example 60, wherein the plurality of sub-signals comprises a first sub-signal and a second sub-signal.

Example 62. The system of any combination of examples 31-61, wherein the processor is further configured to: determine, for a selected frequency of an electrical stimulation signal, a strength-duration curve based on the paresthesia threshold or perception threshold; and determine, based on the strength-duration curve, a set of one or more electrical stimulation parameter values for generating the lower intensity electrical stimulation signal.

Example 63. The system of any combination of examples 31-62, wherein the system delivers the lower intensity electrical stimulation signal to the patient via at least one electrode located near a spine of the patient below a T9-10 spinal disc space in a lateral view.

Example 64. A system of any combination of examples 31-63, wherein the system delivers the lower intensity electrical stimulation signal to the patient via at least one electrode located near a spine of the patient within 2 millimeters of a midline of the spine of the patient in an anterior/posterior or posterior/anterior view.

Example 65. A computer-readable medium comprising instructions that, when executed by a processor, cause the processor to: control a stimulation generator to generate a lower intensity electrical stimulation signal comprising a plurality of pulses; the lower intensity electrical stimulation signal having a stimulation intensity significantly lower than the paresthesia threshold or perception threshold of the patient; and control the stimulation generator to deliver the lower intensity electrical stimulation signal to the patient.

Example 66. The computer-readable medium of example 65, further comprising instructions that, when executed, cause the processor to: control the stimulation generator to generate a first intensity electrical stimulation signal comprising a plurality of pulses; control the stimulation generator to deliver the first intensity electrical stimulation signal to the patient; and control the stimulation generator to titrate from first intensity electrical stimulation signal to the lower intensity electrical stimulation signal.

Example 67. The computer-readable medium of example 66, further comprising instructions that, when executed, cause the processor to: control the stimulation generator to generate a second intensity electrical stimulation signal comprising a plurality of pulses; and control the stimulation generator to deliver the second intensity electrical stimulation signal to the patient; wherein titration from the first intensity electrical stimulation signal to the lower intensity electrical stimulation signal comprises titrating from the first intensity electrical stimulation signal to the second intensity electrical stimulation signal and titrating from the second intensity electrical stimulation signal to the lower intensity electrical stimulation signal.

Example 68. The computer readable medium of example 67, further comprising instructions that, when executed, cause the processor to: control the stimulation generator to generating a third intensity electrical stimulation signal comprising a plurality of pulses; and control the stimulation generator to delivering, by the medical device, the third intensity electrical stimulation signal to the patient; wherein titration from the first intensity electrical stimulation signal to the lower intensity electrical stimulation signal comprises titrating from the first intensity electrical stimulation signal to the second intensity electrical stimulation signal, titrating from the second intensity electrical stimulation signal to the third intensity electrical stimulation signal, and titrating from the third intensity signal to the lower intensity electrical stimulation signal.

Example 69. The computer-readable medium of example 68, wherein the first intensity electrical stimulation signal, the second intensity electrical stimulation signal and the third intensity electrical stimulation signal are different from each other.

Example 70. The computer-readable medium of any combination of examples 65-69, wherein the lower intensity electrical stimulation signal is less than or equal to 60% of at least one of the paresthesia threshold or perception threshold for a patient.

Example 71. The computer-readable medium of any combination of examples 65-70, wherein the lower intensity electrical stimulation signal is less than or equal to 40% of at least one of the paresthesia threshold or perception threshold for a patient.

Example 72. The computer-readable medium of any combination of examples 65-69, wherein the lower intensity electrical stimulation signal is less than or equal to 20% of at least one of the paresthesia threshold or perception threshold for a patient.

Example 73. The computer-readable medium of any combination of examples 65-72, wherein the lower intensity electrical stimulation signal is in the range of about 10% to 80% of at least one of the paresthesia threshold or perception threshold for a patient.

Example 74. The computer-readable medium of any combination of examples 65-73, wherein the lower intensity electrical stimulation signal is in the range of about 20% to 80% of at least one of the paresthesia threshold or perception threshold for a patient.

Example 75. The computer-readable medium of any combination of examples 65-74, wherein the lower intensity electrical stimulation signal is in the range of about 20% to 60% of at least one of the paresthesia threshold or perception threshold for a patient.

Example 76. The computer-readable medium of any combination of examples 65-71 and 73-75, wherein the lower intensity electrical stimulation signal is in the range of about 40% to 60% of at least one of the paresthesia threshold or perception threshold for a patient.

Example 77. The computer-readable medium of any combination of examples 65-76, wherein the lower intensity electrical stimulation signal is in the range of about 20% to 40% of at least one of the paresthesia threshold or perception threshold for a patient.

Example 78. The computer-readable medium of any combination of examples 66-80, further comprising instructions that, when executed, cause the processor to: control the stimulation generator to titrate automatically.

Example 79. The computer-readable medium of any combination of examples 66-78, further comprising instructions that, when executed, cause the processor to: receive an input from the patient to reverse the titration to an earlier intensity electrical stimulation signal; and control the stimulation generator to reverse the titration to the earlier intensity electrical stimulation signal based on the input from the patient.

Example 80. The computer-readable medium of example 79, further comprising instructions that, when executed, cause the processor to control the stimulation generator to reverse the titration only if the patient provides input to reverse the titration during delivery of two consecutive and different of the first intensity electrical stimulation signal, the second intensity electrical stimulation signal, the third intensity electrical stimulation signal and the lower intensity electrical stimulation signal.

Example 81. The computer-readable medium of any combination of examples 66-80, further comprising instructions that, when executed, cause the processor to control the stimulation generator to randomize at least one of an order of titration between electrical stimulation signals, and a time between titrations.

Example 82. The computer-readable medium of any combination of examples 66-80, further comprising instructions that, when executed, cause the processor to control the stimulation generator to deliver electrical stimulation signals in a predetermined order and to titrate between electrical stimulation signals at a predetermined time.

Example 83. The computer-readable medium of any combination of examples 66-82, further comprising instructions that, when executed, cause the processor to determine an ideal intensity based on feedback from the patient.

Example 84. The computer-readable medium of example 83, wherein the feedback from the patient is based on a level of satisfaction of the patient for each intensity electrical stimulation signal.

Example 85. The computer-readable medium of example 84, wherein the level of satisfaction of the patient is based on at least one of whether the patient feels stimulation for each intensity electrical stimulation signal, whether the patient feels stimulation some of the time or all of the time for each intensity electrical stimulation signal, whether the patient is uncomfortable for each intensity electrical stimulation signal, and whether the patient is feeling similar pain relief for each intensity electrical stimulation signal.

Example 86. The computer-readable medium of any combination of examples 83-85, further comprising instructions that, when executed, cause the processor to control the stimulation generator to titrate to the ideal intensity automatically.

Example 87. The computer-readable medium of any combination of examples 65-86, further comprising instructions that, when executed, cause the processor to determine the paresthesia threshold or perception threshold for the patient in a first posture.

Example 88. The computer-readable medium of example 87, further comprising instructions that, when executed, cause the processor to automatically set a predicted paresthesia threshold or predicted perception threshold for the patient in a second posture based on the paresthesia threshold or perception threshold for the patient in the first posture.

Example 89. The computer-readable medium of any combination of examples 87 and 88, further comprising instructions that, when executed, cause the processor to set the predicted paresthesia threshold or predicted perception threshold for the patient in the second posture at about 30% different than the paresthesia threshold or perception threshold for the patient in the first posture.

Example 90. The computer-readable medium of example 89, further comprising instructions that, when executed, cause the processor to adjust the predicted paresthesia threshold or predicted perception threshold for the patient in the second posture based of feedback from the patient.

Example 91. The computer-readable medium of example 90, further comprising instructions that, when executed, cause the processor to adjust the predicted paresthesia threshold or predicted perception threshold for the patient in the second posture automatically.

Example 92. The computer-readable medium of any combination of examples 65-91, wherein the lower intensity electrical stimulation signal has a frequency of about 1000 Hertz.

Example 93. The computer-readable medium of any combination of examples 65-92, wherein the lower intensity electrical stimulation signal has a pulse width of about 90 microseconds.

Example 94. The computer-readable medium of any of examples 65-93, further comprising instructions that, when executed, cause the processor to control the stimulation generator to generate the lower intensity electrical stimulation signal by: generating a plurality of sub-signals; and interleaving the plurality of sub-signals.

Example 95. The computer-readable medium of example 94, wherein the plurality of sub-signals comprises a first sub-signal and a second sub-signal.

Example 96. The computer-readable medium of any combination of examples 65-95, further comprising instructions that, when executed, cause the processor to: determine, for a selected frequency of an electrical stimulation signal, a strength-duration curve based on the paresthesia threshold or perception threshold; and determine, based on the strength-duration curve, a set of one or more electrical stimulation parameter values for generating the lower intensity electrical stimulation signal.

Example 97. The computer-readable medium of any combination of examples 65-96, wherein the stimulation generator delivers the lower intensity electrical stimulation signal through at least one electrode located near a spine of the patient below a T9-10 spinal disc space in a lateral view.

Example 98. A computer-readable medium of any combination of examples 65-97, wherein the stimulation generator delivers the lower intensity electrical stimulation signal through at least one electrode located near a spine of the patient within 2 millimeters of a midline of the spine of the patient in an anterior/posterior or posterior/anterior view.

Example 99. A method comprising: determining a paresthesia threshold or perception threshold of a patient in a first posture; determining a predicted paresthesia threshold or predicted perception threshold of the patient in a second posture based on the paresthesia threshold or perception threshold of the patient in the first posture.

Example 100. The method of example 99, wherein the predicted paresthesia or predicted perception threshold of the patient in the second position is about 30% different than the paresthesia threshold or perception threshold for the patient in the first posture.

Example 101. The method of example 100, further comprising adjusting the predicted paresthesia threshold or predicted perception threshold for the patient in the second posture based of feedback from the patient.

Example 102. The method of example 101, further comprising automatically adjusting the predicted paresthesia threshold or predicted perception threshold for the patient in the second posture.

Various aspects of the disclosure have been described. These and other aspects are within the scope of the following claims.

What is claimed is:

1. A method comprising:
   generating, by a medical device, three or more electrical stimulation signals each comprising a plurality of pulses and each having a different stimulation intensity, the three or more electrical stimulation signals comprising a lower intensity electrical stimulation signal, wherein the lower intensity electrical stimulation signal has a stimulation intensity that is equal to or less than 40% of a paresthesia threshold or perception threshold of a patient; and
   delivering, by the medical device, the three or more electrical stimulation signals to target tissue of the patient,
   wherein delivering the three or more electrical stimulation signals to the target tissue of the patient comprises titrating between the three or more electrical stimulation signals in a progressively less intensive order or a random order.

2. The method of claim 1, further comprising:
   receiving an input from the patient to reverse titrating to an earlier intensity electrical stimulation signal; and
   reverse titrating to the earlier intensity electrical stimulation signal based on the input from the patient.

3. The method of claim 1, further comprising:
   receiving a first input from the patient to reverse titrating to an earlier intensity electrical stimulation signal;
   continue titrating to a next intensity electrical stimulation signal;
   after titrating to the next intensity electrical stimulation signal, receiving a second input from the patient to reverse titrating to the earlier intensity electrical stimulation signal; and
   based on receiving both the first input from the patient and the second input from the patient, reverse titrating to the earlier intensity electrical stimulation signal.

4. The method of claim 1, wherein the lower intensity electrical signal is less than or equal to 20% of at least one of the paresthesia threshold or perception threshold of the patient.

5. The method of claim 1, wherein the lower intensity electrical signal is within the range of about 20% to less than 30% of at least one of the paresthesia threshold or perception threshold of the patient.

6. The method of claim 1, further comprising determining an ideal intensity of an electrical stimulation signal based on feedback from the patient.

7. The method of claim 6, wherein the feedback from the patient is based on a level of satisfaction of the patient for each intensity electrical stimulation signal.

8. The method of claim 1, wherein each stimulation intensity of the three or more electrical stimulation signals comprises 80% of the paresthesia threshold or the perception threshold of the patient, 60% of the paresthesia threshold or the perception threshold of the patient, 40% of the paresthesia threshold or the perception threshold of the patient, or 20% of the paresthesia threshold or the perception threshold of the patient.

9. The method of claim 1, wherein the three or more electrical stimulation signals comprise four electrical stimulation signals.

10. A system comprising:
a stimulation generator configured to generate and deliver electrical stimulation therapy to a patient via at least one electrode; and
a processor configured to control the stimulation generator to:
generate three or more electrical stimulation signals each comprising a plurality of pulses and each having a different stimulation intensity, the three or more electrical stimulation signals comprising a lower intensity electrical stimulation signal, wherein the lower intensity electrical stimulation signal has a stimulation intensity that equal to or is less than 40% of a paresthesia threshold or perception threshold of the patient; and
deliver the three or more electrical stimulation signals to target tissue of the patient,
wherein to deliver the three or more electrical stimulation signals to the target tissue of the patient the processor is configured to titrate between the three or more electrical stimulation signals in a progressively less intensive order or a random order.

11. The system of claim 10, wherein the processor is further configured to:
receive an input from the patient to reverse the titration to an earlier intensity electrical stimulation signal; and
control the stimulation generator to reverse the titration to the earlier intensity electrical stimulation signal based on the input from the patient.

12. The system of claim 10, wherein the processor is further configured to:
receive a first input from the patient to reverse titrate to an earlier intensity electrical stimulation signal;
continue to titrate to a next intensity electrical stimulation signal;
after titrating to the next intensity electrical stimulation signal, receive a second input from the patient to reverse titrate to the earlier intensity electrical stimulation signal; and
based on receiving both the first input from the patient and the second input from the patient, reverse titrate to the earlier intensity electrical stimulation signal.

13. The system of claim 10, wherein the lower intensity electrical stimulation signal is less than or equal to 20% of at least one of the paresthesia threshold or perception threshold for a patient.

14. The system of claim 10, wherein the lower intensity electrical stimulation signal is in the range of about 20% to less than 30% of at least one of the paresthesia threshold or perception threshold for a patient.

15. The system of claim 10, wherein the processor is further configured to determine an ideal intensity based on feedback from the patient.

16. The system of claim 15, wherein the feedback from the patient is based on a level of satisfaction of the patient for each intensity electrical stimulation signal.

17. The system of claim 10, wherein each stimulation intensity of the three or more electrical stimulation signals comprises 80% of the paresthesia threshold or the perception threshold of the patient, 60% of the paresthesia threshold or the perception threshold of the patient, 40% of the paresthesia threshold or the perception threshold of the patient, or 20% of the paresthesia threshold or the perception threshold of the patient.

18. The system of claim 10, wherein the three or more electrical stimulation signals comprise four electrical stimulation signals.

19. A non-transitory computer-readable medium comprising instructions that, when executed by a processor, cause the processor to:
control a stimulation generator to generate three or more electrical stimulation signals each comprising a plurality of pulses and each having a different stimulation intensity, the three or more electrical stimulation signals comprising a lower intensity electrical stimulation signal wherein the lower intensity electrical stimulation signal has a stimulation intensity that is equal to or less than 40% of a paresthesia threshold or perception threshold of the patient; and
control the stimulation generator to deliver the three or more electrical stimulation signals to target tissue of the patient,
wherein the instructions cause the processor to control the stimulation generator to deliver the three or more electrical stimulation signals to the target tissue of the patient by titrating between the three or more electrical stimulation signals in a progressively less intensive order or a random order.

* * * * *